US009746406B2

(12) United States Patent
Flock et al.

(10) Patent No.: US 9,746,406 B2
(45) Date of Patent: Aug. 29, 2017

(54) FLOW TEST MACHINE AND AN ASSOCIATED MEASUREMENT METHOD, AS WELL AS AN ASSOCIATED CLEANING PROCESS

(71) Applicant: Zwick GmbH & Co. KG, Ulm (DE)

(72) Inventors: Marcus Flock, Achstetten (DE); Franz Ganser, Laupheim (DE); Ulrich Kindermann, Erbach (DE); David Völzke, Fellbach (DE)

(73) Assignee: ZWICK GMBH & CO. KG (DE)

( * ) Notice: Subject to any disclaimer, the term of this patent is extended or adjusted under 35 U.S.C. 154(b) by 2 days.

(21) Appl. No.: 14/868,230

(22) Filed: Sep. 28, 2015

(65) Prior Publication Data

US 2016/0091404 A1 Mar. 31, 2016

(30) Foreign Application Priority Data

Sep. 29, 2014 (DE) .................. 10 2014 114 117

(51) Int. Cl.
*G01N 11/02* (2006.01)
*B08B 9/04* (2006.01)
(Continued)

(52) U.S. Cl.
CPC ............... *G01N 11/02* (2013.01); *B08B 9/04* (2013.01); *G01N 11/04* (2013.01); *G01N 3/10* (2013.01); *G01N 33/442* (2013.01)

(58) Field of Classification Search
CPC .......... G01N 11/02; G01N 11/04; G01N 3/10; G01N 33/442; B08B 9/04
(Continued)

(56) References Cited

U.S. PATENT DOCUMENTS 3,625,050 A 12/1971 Noetzel et al.
4,574,623 A 3/1986 Neumann
(Continued)

FOREIGN PATENT DOCUMENTS

DE 1773874 7/1968
DE 2140619 2/1973
(Continued)

OTHER PUBLICATIONS

ASTM D 1238 Testing standard, ASTM International, 2004.
(Continued)

*Primary Examiner* — Daniel S Larkin
(74) *Attorney, Agent, or Firm* — Pate Peterson PLLC; Brett Peterson

(57) ABSTRACT

A flow test machine 2 which, for example, is able to be used for viscosity tests on plastics, comprises a test piston 4, a test channel 38, at least one test weight 72 and a drive unit 92. The test piston 4 is able to move through the test channel 38 by means of a weight force 79 of the test weight 72. The test weight 72 is able to be loaded by an actuating additional force 108, 108' by means of the drive unit 92 between a starting position 151 and an end position. The actuating additional force 108 enables a movement of the test piston 4 in the direction of the weight force 79, said movement being accelerated in comparison with an effect of the weight force 79. In a melt viscosity test, after a heating step, a thermoplastic plastic is pressed through a test channel 38 by a test piston 4. In a measurement preparation step and/or a cleaning step, the test mass is lowered along a weight force direction 79 under the influence of an actuating additional force 108, 108'. In a method for cleaning, a cleaning step is undertaken by means of an actuating additional force 108, 108' from the drive unit 92, said drive unit 92 serving to drive a test piston movement during a melt viscosity test.

20 Claims, 8 Drawing Sheets

(51) Int. Cl.
*G01N 11/04* (2006.01)
*G01N 3/10* (2006.01)
*G01N 33/44* (2006.01)

(58) Field of Classification Search
USPC ............... 73/54.11, 54.13, 54.14, 54.18
See application file for complete search history.

(56) References Cited

U.S. PATENT DOCUMENTS

| | | | |
|---|---|---|---|
| 4,882,930 | A | 11/1989 | Nagy et al. |
| 5,008,081 | A | 4/1991 | Blau et al. |
| 5,016,467 | A | 5/1991 | Marcec et al. |
| 5,347,851 | A * | 9/1994 | Grudzien, Jr. ........ G01L 9/0077 374/56 |

FOREIGN PATENT DOCUMENTS

| | | |
|---|---|---|
| DE | 7640849 | 8/1977 |
| DE | 2735224 | 2/1979 |
| DE | 102009042478 | 3/2011 |
| EP | 0278683 | 8/1988 |
| EP | 2480863 | 6/2010 |
| JP | S58113734 | 7/1983 |
| WO | WO 2008/049051 | 4/2008 |

OTHER PUBLICATIONS

Bulletin 131-A, Tinius Olsen, 2003.
Bulletin 131-D, Tinius Olsen, 2012.
DIN EN ISO 1133-1 Testing standard, DIN Deutsches Institut fur Normung e. V., Mar. 2012.
DIN EN ISO 1133-2 Testing standard, DIN Deutsches Institut fur Normung e. V., Mar. 2012.

* cited by examiner

FLOW TEST MACHINE AND AN ASSOCIATED MEASUREMENT METHOD, AS WELL AS AN ASSOCIATED CLEANING PROCESS

PRIORITY

The present application claims the benefit of DE 10 2014 114 117.2, filed Sep. 29, 2014, which is herein incorporated by reference in its entirety.

In the testing of thermoplastics, flow test machines, also referred to as a capillary viscometers by some manufacturers, are used, with which fusible or sliding plastics in particular are tested on their flow behavior during pressing. Some of the testing machines work with the acquisition of melt mass flow rates; others work with melt volume flow rates. Melt mass flow rates and melt volume flow rates can be converted into each other taking into account different test conditions for a known density of the melt. In both flow rate measurements, time is always a measureable entity. The present invention therefore relates to a flow test machine, in particular for viscosity tests, for example of plastics, a method for testing of viscosities, as well as a method for cleaning a flow test machine.

PRIOR ART

Flow test machines are used for example, for comparative studies of plastics, which is why different manufacturers have endeavored for long periods of time to provide flow test machines, by which findings on the flow characteristics of a plastic or a mixture of plastic, in particular under selected test parameters, can be obtained.

Therefore, a melt viscosity test device is presented, among others, in DE 2 140 619 A (Applicant: Badische Anilin- & Soda-Fabrik A G; Publication date: 02.22.1973). According to DE 2 140 619 A, a melt viscosity test device should include a separable weight, a "plug weight" and "measuring weight", used during the respective phases of a test. The composition of both weights is used to plug the measurement sample in the test channel and to clean the test channel after a successful measurement cycle, wherein, however, only the measuring weight can be chosen as the load weight. A lift device is provided which should, however, work with chains and therefore is probably not able to be used for applying a weight force with an additional force. A compression die using a geared motor of the lift device and using the weights should be retracted several times into the test channel during plugging. Decoupling of plug weight and measuring weight should happen after a period of heating-up time, wherein the plug weight is held in place by a motorized latch. The measuring weight and the compression die can together be moved downward on a transverse bar. At a switching position, the transverse bar can be moved by the geared motor of the measuring weight, at which point the measuring gear is released. The measurement is to be terminated at a so-called "bottom dead center". Using the geared motor, the compression die should start being moved upward again. The weights, as stated previously, are to be merged back together, namely on a "top dead center" of the compression die. Both weights are then jointly used for a cleaning cycle to clean the test channel and the shaft of the compression die of sample residues. Similar designs are set forth in DE 1 773 874 A (Applicant: Badische Anilin- & Soda-Fabrik A G; Publication date: 01.13.1972) and in U.S. Pat. No. 3,625,050 (Patentee: Badische Anilin- & Soda-Fabrik A G; Issue Date: 07.12.1971).

The German utility model DE 76 40 849 U 15 (Applicant: Göttfert-Feinwerk-Technik GmbH; Publication date: 08.11.1977) relates to a capillary rheometer for the measurement of viscosity of rubber and thermoplastics. The test shall be performed with a variable speed drive motor for moving the test die, wherein a control allows you to take measurements in three different operating modes in conjunction with a load cell and a melt pressure sensor disposed upstream of the nozzle. The operating modes are a constant test load on the test die, a constant mass pressure against the nozzle or a constant speed of the extrudate escaping from the nozzle. In addition, a speed regulator is provided to adjust a velocity target value.

The document DE 27 35 224 A1, (Applicant: Instruments S.A.; Publication date: 02.15.1979) refers to a capillary viscometer to examine the suitability of polymers for injection molding. A shear chamber should be arranged upstream of a capillary, before which should in turn be a pressure chamber for raw material. For shearing and heating up of the material, the piston is put into rotation. Softened material is displaced into the capillary by the piston through means of pressure cylinders from the storage chamber.

In European Patent EP 2 480 863 B1 (Owner: Zwick GmbH & Co. KG; Date of Priority: 09.24.2009) as well as the German patent application DE 10 2009 042 478 A1 Patent Applicant: Zwick GmbH & Co. KG; Date of Priority: 09.24.2009), a force transducer for testing equipment to conduct testing with a load cell is described, wherein, among other things, the load cell is surrounded by a heat insulating shield body. The figures show details which can be built into flow test machines.

Test conditions for testing of thermoplastics, in particular for determining a melt mass flow rate and/or a melt volume flow rate are laid out in the standards: ISO 1133-1: 2011 and ISO 1133-2: 2011. In the United States of America, the standard ASTM D 1238 shall apply. The testing conditions laid down in said standards, in particular with respect to geometry, dimensions and test conditions, are considered fully included in the scope of disclosure of this application. Through compliance with standards, comparable results can be obtained, for example in the technical field of quality assurance due to the current standardization.

Reference should also be made to two brochures from Tinius Olsen, Inc., namely the "Bulletin 131-A" (dated June 2003) and the "Bulletin 131-D" (dated August 2012), in which devices for performing material tests in accordance with North American standards are presented.

SUMMARY OF THE INVENTION

A flow test machine which satisfies diverse contemporary standardization requirements would be desirable. Such a flow test machine could be used in different countries in which these different standards apply. The flow test machine should allow a particularly efficient implementation of flow tests according to another aspect. The present invention is thus based on the underlying consideration of providing a test machine, where the material tests or series of material tests, in particular of flowable thermoplastics, are reproducible, particularly in accordance with feasible standardization. A particularly advantageous flow test machine would therefore be one which can both perform tests according to various standardization specifications as well as perform tests with very short cycle times. This is especially desirable in a sequence of material tests, wherein it is of course clear to the person skilled in the art that some of the specifications of a standard in turn contravene a short test time.

DESCRIPTION OF THE INVENTION

The object of the invention is solved by a flow test machine which may include a test piston, a test channel, at least one test weight, and a drive unit such as an hydraulic or a pneumatic actuator. A weight force of the test weight is able to be applied to the test piston and the test piston is able to move through the test channel with the aid of the weight force. The test weight is able to be raised from the drive unit. Between at least one first position of the test piston; a starting position, and at least one second position of the test piston; an end position, the weight force is able to be applied by means of the drive unit with an additional actuating force for a movement of the test piston in a first direction of a force with the movement being accelerated in comparison to an effect of the weight force alone. The weight force may be applied alone on at least one stretch and preferably on at least two partial stretches that are spaced apart from one another along the test channel. An appropriate procedure for conducting a melt viscosity test may include, in a first step; a heating step, heating a test material and, in a measurement step, the heated test material may, in a flowing state as a result of the influence of heat, be pressed by a test piston through a test channel. In a measurement preparation step after a melting time, and/or in a cleaning step which takes place in movement direction continuity after the measurement step, the test material may be lowered along a weight force direction under the influence of an additional actuating force which is in the same direction as a weight force direction. To achieve comparable measurement results that are as good as possible with a flow test machine a flow test machine may be cleaned by using a cleaning piston and a test cylinder of the flow test machine and an additional actuating force, formed or created from a drive unit of the flow test machine which in a melt viscosity test drives a movement of a test piston at least through a partial stretch of the test channel of the flow test machine, moves test material in the direction towards a press-out nozzle. Advantageous developments can be taken from the dependent claims.

The melt mass flow rate and the melt volume flow rate are material properties, which among other things depend on the chemical composition of the examined plastic or the quality of the used plastic. Plastics are often present as polymers, whose fluidity can be slowed by chain lengths or even by a number of bridging bonds between polymer chains. For many types of plastics, values of flow rates that suggest an acceptable quality level of the plastic, are stored in tabular form, for example in relevant manuals or manufacturer databases. Deviations from tabulated stored values may also indicate damage and/or foreign matter in a thermoplastic material to be tested. Changes in a structure of plastics, such as a fracture in polymer chains of plastic molecules, can be caused, for example, by aging, high-energy, especially ultraviolet radiation, mechanical stresses or by short-term overheating. In known plastics, the ascertained melt mass flow rates and melt volume flow rates, especially without conversion, are used as a quality assurance parameter. Measured flow times are a measure of the viscosity of the investigated plastics. The viscosity is predictable using evaluated measurement data of a flow test machine. In other words, the reciprocal of viscosity, the fluidity, is a measure of the flow of a fluid. With respect to many plastics to be examined, the rule is that the viscosity of a fluid decreases with an increase in temperature of the fluid.

A flow test machine, often also referred to as a capillary rheometer, is a measurement device with which the flow rates of liquid materials can be measured, such as, in particular, molten plastics. The flow test machine is used for the measurement of a deformation and/or flow property of materials. It may be, material properties, such as viscosity or parameters derived from viscosity, of materials in a liquid state may in particular be determined. The flow test machine is designed for the determination of flow properties of thermoplastics. Thermoplastics are materials in a free-flowing state of aggregation that exist in a first temperature range, which is limited in particular by the thermal decomposition temperature of the plastic to higher temperatures. In principle, some thermally stable plastics can also exist as a vapor, whose viscosity properties can be examined in a flow test machine. Flow test machines are particularly suitable for the study of condensed matter. At lower temperatures, a second temperature range is associated with the first temperature range, wherein thermoplastic plastics are vividly ductile. In a third temperature range that is below the second temperature range, thermoplastic plastics are elastic. At a fourth, even lower temperature range, for example, below 20° C., many plastics are structurally sound and can show, under examination at lower temperatures, an increase in brittleness. Due to the particularly high forces that are generally required for compression of elastic or solid plastics, flow test machines are rarely used for such available plastics. After a plastic deformation, the embossed form of the plastic remains. Elastic deformation relaxes when the shaping force is turned off. Numerous polymeric plastics such as polymers based on units of olefins, styrenes, amides, lactates, methacrylates, carbonates, ethylene terephthalates or vinyl chlorides possess thermoplastic properties.

The flow test machine has a test channel. The test channel is a, in particular cylindrical, recess, such as a hole in a solid, pressure-resistant and preferably chemically inert material, such as for example a steel. The test channel has a channel diameter and a channel length, wherein the channel length is preferably larger than the channel diameter. The test channel is advantageously cylindrical. The test channel can be filled with a sample of the material to be tested. The material sample can be present, for example, as a rod, as a granulate or a powder with a diameter smaller than the diameter of the channel, or even as a liquid. The size of the diameter of the test channel promotes filling of the test channel, for example with a solid, granulate-like material sample. The channel length of the test channel is preferably able to be aligned along a vertical.

At least one test piston is allocated to the test channel. The test piston has a test piston diameter that is smaller than the diameter of the test channel, so that the test piston is able to be inserted into the test channel. A length of the test piston can be greater than or equal to a length of the test channel. The test piston is preferably arranged in a position of use along the test channel, in particular along a central axis of the test channel. At least one intercept of the central axis can also be described as the test axis. A test piston axis lies at least in one measuring cycle on the central axis of the test channel. The test piston can be adjustable in relation to the test channel. Within an area of the test piston, preferably one, in particular cylindrical, end area, where a press surface is located, the test piston can rest extensively against an inner wall of the test channel in a peripherally fluid-tight manner. According to one aspect, the test piston is formed as a fixed rod. It is possible that at least one cavity is provided in the test piston, for example, in order to reduce the weight of the test piston. The test piston should be designed to be stiff against bending. A test force is able to be transferred from a first end area of the test piston to a second end area of the test piston, preferably without loss.

There is at least one test weight provided. The test weight is used to provide a defined weight force. The test weight has a given mass. The test weight can be composed of stackable test weight bodies. Cylinder discs as test weight bodies are favorable for centered provision of a summary weight force. At the opposite surfaces of the cylinder discs, a rest area and a center area can be provided, wherein a first centering area of a first test weight body fits into a second centering area of a second test weight body.

A mass of the test weight is set in accordance with standards usually depending on the material to be tested. The mass of a test weight can be, for example, 20 kg (kilograms). Test weights can, however, also be less than 1 kg in weight. Because the gravitational acceleration is dependent on the location of the measurement, the weight force at the respective location of the measurement can be considered for further increasing measuring accuracy, for example by correction weights in the per-mil range of the respective mass. A first body, which has a weight and can therefore be described as a test weight, is the test piston. A, in particular first, test weight body can be moved in a form-fitting and force-fitting connection with the test piston, in particular with a first end area of the test piston. Another test weight body, such as a second test weight body, can be mounted on the test weight bodies, especially the first test weight body. The weight force of the test weight body affects the test piston, in particular along a central axis of the test piston. The test weight can push the test piston into the test channel. The weight force of a mounted test weight piston contributes vectorially to the force that moves the test piston. The test piston is able to move through the test channel by a weight force which exceeds, in particular, at least a frictional force between the test piston and test channel. A first operational state of the flow test machine operates preferably with the test weight, wherein the first operational state is assumed before a measuring operational state exists.

The flow test machine is equipped with a drive unit. The drive unit may include, for example, a hydraulic or a pneumatic actuator. It is also possible to use electromotive drives to generate forces in the test machine. The actuator can be formed with a, in particular dual-controllable, hydraulic or pneumatic cylinder. Through the drive unit such as the hydraulic or pneumatic actuator, a predetermined force within tolerance limits is applied, for example via a force control unit, starting from a source pressure of a hydraulic fluid or a pressurized air source. According to a further aspect, the drive unit provides at least one travel path on which the force of the drive unit is available. Along the travel path, a control can stabilize the force provided by the drive unit on a constant amount of power. Preferably, a travel path of the drive unit extends along the central axis of the test channel.

According to one aspect, the drive unit can move the test piston, especially in the test channel, against a gravitational force, in particular of the test weight. In other words, the test weight is able to be lifted by the drive unit, wherein a movement direction contrary to the gravitational force is possible. It is, however, also possible to lower the test weight by the drive unit. In another configuration, it is possible, in particular additionally possible, to reduce a weight force of the test weight by the drive unit. If a force resulting from the drive unit is exerted on the test piston, the test piston and the drive unit are in a preferably mechanical connection. Alternatively, it is also possible to provide a magnetic force coupling for force transmission, for example to prevent possible transmission of vibrations to the test piston. It can also be said that the test weight and the drive unit are in a force coupling connection. The existence of a force coupling connection can be described as a drive state. In the drive state, an actuating additional force generated by the drive unit adjoins the test piston. The first operating state can be a drive state. In an additional operating condition or to approach this operating state, the force coupling connection is releasable, so that there is no longer any connection between drive unit and test piston, so no actuating additional force exists.

Though primarily the movements of the test piston are considered in relation to the preferably statically arranged test channel, embodiments are also possible in which the drive unit causes or supports a relative movement between test piston and test channel, e.g. by a connection to the test channel or even according to a type of pincer movement.

With respect to the test channel, several positions can be allocated to the test piston, which are described in greater detail below. A first position can be described as a starting position. A starting position can, for example, be taken by the test piston when an end area of the test piston, in particular the pressing surface of the test piston, is allocated to an end area of the test channel, especially a filling opening of the test channel. The actuating additional force deploys in the starting position. From the starting position, the test piston is able to be accelerated by the actuating additional force. The test piston accelerates from the starting. A starting position can also be a rest position of the test piston over a fixed interval of time. In the rest position, the test piston is held in position by the volume that occupies a plastic filling in the test channel, for example. A second position is an end drive position. An end drive position can have a spacing of the pressing surface to the starting position along the test channel toward the weight force of the test weight. A partial stretch, such as a first partial stretch, lies between a starting position and an end drive position along the test channel. The supply of the actuating additional force ends in the end drive position. The starting position and the end drive position are arranged along the test axis. Several starting and end drive positions of the test piston can also be provided. Between the starting position and the end drive position, the test piston can be loaded by both the weight force as well as by an actuating additional force. It can also be said that there is a drive state. The test piston is powered by the actuator. The actuating additional force is applied by the drive unit. Thus, at least the weight force and the vectorially parallel, actuating additional force affect the test piston in this phase. If the movement of the test piston, with the simultaneous action of the weight force and the actuating additional force, is compared with a movement of the test piston which is only under the influence of the weight force, the test piston executes a more rapid movement with the actuating additional force, in particular in an operating state. The test piston travels a distance within the test channel between the first position and the second position in a shorter time, which is caused by the supplied actuating additional force. If there is a flowable plastic in the test channel, a plastic mass that can be displaced or pressed out by the actuating additional force in a unit of time such as one second, in other words a displaceable plastic mass, is larger than the plastic mass that is able to be displaced under the influence of the weight force of the test weight. The extrudable plastic mass leaves under the influence, in other words under the pressure, of the test piston the test channel, in particular from an end of the test channel located opposite the fill opening (also called filling opening) of the test channel. The measurement of the flow time in the flow test is carried along a predetermined stretch area of the test channel, which may also be referred to as a test stretch, testing stretch or measuring stretch. The starting position and the end drive position are outside or at the edge of the test stretch. Due to the faster movement by means of actuating additional force, at least the test stretch can be reached more quickly by the test piston.

The cycle times during flow tests can thus be shortened. With flow test machines designed in this way, more test cycles can be carried out in a unit of time. Time efficiency when performing flow tests is increased.

During the measuring process, the piston covers a measurement section. According to a preferred embodiment, after the measurement path, i.e. spatially separated from the first partial stretch, the test piston can have a further starting position from which the actuating additional force can be applied to the test piston again. At least one second partial stretch can be connected to the second starting position. On the second partial stretch, the additional actuating force acts on the test piston. In this case, the test piston in particular executes a more rapid movement along the test channel. The second partial stretch extends to a second end drive position. In all partial sections in which the test piston performs the movement under the action of the actuating additional force, process time is able to be saved, resulting in short time steps. It is possible, on a second partial stretch, to apply a greater actuating additional force than on a first partial stretch and thus to achieve a further reduction in cycle time.

A melt viscosity test for determining material properties that provide information about or of the flow behavior, for example of thermoplastics, can be performed in a flow test machine, in particular in a flow test machine described above. The material to be tested in a predetermined amount of material is heated in a first step. By means of a heat source, the test material is brought in particular to a temperature which is in a first or in a second temperature range. The heating step converts the material into a compressible state if an initial consistency of the test material does not already have sufficient flowability. The heating may take place in particular in a uniformly heated test channel. During the heating step, for example, air bubbles can escape from the material. Cavities in the material, which may affect the measurement process, are at least reduced. The test material exists, due to the influence of heat, in a flow state, in particular at the flow test temperature. A flow state is a state in which a material can be caused to flow, for example by removing a barrier or closing plate obstructing the flow.

The flow test temperature may be above the melting point of the material to be tested. The decomposition temperature of the test material should remain as unmatched as possible during the execution of the test method. Temperatures between 180° C. and 300° C., for example, have proved to be expedient for many plastics. For polyethylenes, a typical flow test temperature is 190° C. Suitable flow test temperatures for individual plastics can be derived from data from plastics manufacturers. At the end of the heating step, the test mass can be held for a certain period of time, the melting time, at a constant temperature, the flow test temperature, in order to distribute the heat uniformly in the mass. It can also be said that the heating step may include a warm-up time and a melting time. The test mass will melt and homogenize itself or is at least plastically deformable so that it can be pressed through the test channel. A melting time of the test mass for many plastics can take six to seven minutes. The test mass can also be known as test material that exists in particular in a test area, preferably in a region for experiments.

After the heating step, in particular after a melting time, the testing of the test mass is initiated. This phase of the heating step can also be characterized as a measurement preparation step. The test piston, for example, moves in the measurement preparation step from a first position to a second position. A first part of the test mass is pressed out of by the test piston and separated from the test mass in the measurement preparation step, especially in a short time, that is to say quickly, for example, within just five seconds. There is a displacement of the test material. The displacement guides the test mass towards an outlet opening of the test channel. The outlet opening is located at a vertical arrangement of the test channel under a filling opening of the test channel. There is—in other words—a lowering of the test mass. In the measuring preparation step, the actuating additional force is coupled to the test piston. The actuating additional force acts along a weight force direction. The actuating additional force is directed in the same direction as the weight force direction, whereby the test piston can be driven. By force coupling, a movement of the test piston is effected, which is, in particular, faster than without force coupling.

The measurement, in particular of a press-out time, takes place after the measurement preparation step with a test mass from an average stretch range of the test channel after the filling of the test channel. During a measuring step, the test mass is forced through the test channel by the test piston. The test piston thus exerts a force on the heated mass, which had been heated in the heating step. The force has the effect of the test mass exiting from at least one opening of the test channel.

During the measuring step, a predetermined force, which is exerted only by the weight, acts—in a first measurement operating state—on the test piston. A connection between the test piston and the drive unit is interrupted, there may be no flow of force. The test weight offers the only driving force. The test piston in the test channel can be stalled as a result of counter-forces, caused for example by friction and/or viscosity effects of the test mass, if the test weight is dimensioned to be too low. A resistance counteracts the weight force of the test weight. A very high level of accuracy can be achieved, however, in a second possible measuring operating condition in which an actuating additional force drives a test piston during the measurement step, in particular, in addition to a weight force, whereby an effective test weight is provided. In one setting, the actuating additional force is adjusted to compensate for the resistance that counteracts the weight force. In such a case, the weight force (completely) generates the propulsion force on the test piston.

After the measurement step, a cleaning step can take place. The cleaning step serves, for example, to expel test material which is still located in the test channel after the measurement step. Test material remains are removed from the test channel before a next melt viscosity test, especially before possible deposits could set in the test channel. The actuating additional force is coupled in the measuring step to the test piston. The test piston maintains the movement direction of the measurement step, wherein an acceleration of the test piston and thereby a faster execution of the cleaning step are carried out. There is therefore movement direction continuity, in which no reversal of direction of movement is carried out. The actuating additional force is rectified to the weight force direction. More test material is lowered. The measurement preparation step and the cleaning step can also be combined individually or together with the measurement step in the movement direction continuity. Thus, flow tests can be undertaken to a high level of precision.

A flow test machine should be cleaned during use or after each test, in order to obtain useful measurement results, which can take more time to complete than the time for the actual flow test. An inventive cleaning method able to be implemented very quickly can be run, for example, before or after melt viscosity tests. The cleaning process works with at least one cleaning piston. The cleaning piston is able to be inserted in particular in the place of a test piston into the flow test machine, particularly into a test channel of the flow test machine. The flow test machine has a test cylinder. The test cylinder is present, for example, as a component of a drive unit of the flow test machine that is able to be loaded hydraulically or pneumatically for the generation of a mechanical movement in a test flow method. The drive unit drives the test piston in a melt viscosity test. The drive unit enables freedom of movement of the drive unit, in particular for a, preferably straight, drive stretch movement. A force provided by the drive unit can move the test piston in the test channel. The drive unit can carry the test piston at least through a partial stretch of the test channel. The test channel can be limited at one end by a press-out nozzle. The press-out nozzle has at least one nozzle opening. The press-out nozzle is designed in such a way that it withstands at least one force to the test channel applied, such as the weight force. Preferably, a movement in a direction towards the press-out nozzle is powered. The test piston is therefore moved to a press-out nozzle. It is particularly advantageous if, in the cleaning method, the drive unit applies an actuating additional force to carry out the cleaning. The cleaning piston is moved by the drive unit on a path of the test piston through the test channel. Through the use of the drive unit of the flow test machine while executing the cleaning method, impurities that can cause potential errors during flow tests are more effectively eliminated, whereby the cycle time is further improved. In particular, series tests of, for example, different polymers or degrading thermoplastics must be repeated less often to obtain statistically trustworthy measurement results.

Below, advantageous embodiments and aspects of particular developments are outlined, which in of themselves, both individually and also in combination, may also disclose inventive aspects.

On the drive unit a coupling unit can be provided in accordance with an advantageous embodiment. A coupling unit serves to provide a frictional connection. The coupling unit can be arranged in the drive unit. Preferably, the coupling unit is a unit between a test cylinder and a test piston. Switchable components, particularly components that can be applied, such as claws, of the coupling unit are assigned to the drive unit. The coupling unit makes it possible to take the actuating additional force off the test piston. In particular, in a first switching position, there is a separation of actuating additional force from the test piston. According to another aspect, a coupling unit serves to release an existing frictional connection. In a second switching position of the drive unit, a transfer of the actuating additional force from the drive unit can be enabled. The actuating additional force is able to be supplied to the test piston in the second switching position via the coupling unit. The coupling unit allows a precise coupling or uncoupling of the drive unit to the test piston or to a test weight, in particular a test weight body. The coupling unit works or functions in a slip-free manner. The coupling unit is suitable for transmitting the actuating additional force. In accordance with the switching position of the coupling unit, thus, depending on the switching position of the coupling unit, an actuating additional force on the piston to be actuated is forwarded.

The test piston can have a test piston head. Those parts of the test piston which remain, if necessary, with other parts of the test piston connected to the test piston head, outside of the test channel, are known as the test piston head, if the test piston is driven in the channel along a length corresponding to the channel length of this test channel. A particularly good orientation of the test piston is achievable if a diameter of test piston head is greater than the diameter of the test channel. The test piston head has a first coupling region. The coupling region is connectable to the drive unit. The test piston head has a support area for a test weight, especially for a test weight body. The support area and the coupling region are advantageously directly next to each other, adjacent in the region of the test piston head. The support area exists in the area of one end of the test piston, preferably forms the end of the test piston, and serves for assembly with a centering area of a test weight body. The piston, just as the test piston, preferably moves via the interaction of a force into one of its end areas. The movement of a piston is spear-like.

At least one service piston can also be provided as a component of the flow test machine. The cleaning piston is a kind of service piston. Along with the cleaning piston, for example, brush and/or cloth parts are moveable in the test channel along the channel length, particularly on a test channel surface. A compression piston can, however, also be present as a further or other service piston. With the compression piston, test material that was filled for example as granulate or powder in the test channel can be compressed. In a mode of operation or type of use of the flow test machine, the test piston also can be used as a compression piston. At least one first compression step can be carried out with a test piston. A service piston can be equipped, for example, with a longitudinal vibrator or a heating element. A service piston can have a vent channel for the test channel. The service piston has a head region. The head region is destined to remain outside of the test channel. A second coupling region is located on the head area of the service piston. In particular, at least one of the coupling regions has a shape which provides at least one connection surface. The design of the shape allows a frictional connection between the drive unit and the coupling region of the associated piston (test or service piston). A frictional and/or positive connection is able to be formed by a design of a region between the drive unit and a piston like the test piston or the cleaning piston. The shape of the coupling region is preferably connectable to a shape of a receiving area of the drive unit. The test piston can thus replace this service piston quickly. By simplifying the operation, the cycle time for carrying out two tests successively can be increased.

Flow tests can be carried out by an user extremely rapidly with a flow test machine as well, if the drive unit has a switchable bracket. The bracket can be switchable by an actuator. The bracket serves to receive the test or the service piston. The bracket can be switched into a release position. In the release position, the test piston or service piston, situated in the respective bracket, can be removed or deposed. The bracket can be shifted into a closed position. The bracket can be connected, for example, to the head of the test piston. In the closed position, the piston, which is located in the bracket, is connected frictionally to the drive unit, preferably also with directional tightness. The bracket may comprise a clamping unit. Particularly advantageous for determining a position, in particular of a test piston, is a clamping unit, which is designed as a centering unit based on a test piston axis. From another point of view, it can also be said that the clamping unit can also provide a centering with respect to the central axis of the test channel. The central axis, for example with a circular cross-section of the test channel, passes through the center of the cross-sectional circle. In other words, the clamping unit serves for reproducible orientation of the test piston. Because of the centering clamping unit, a closed position is able to be assumed without transverse forces or tilting forces acting on the test piston. In particular, the test piston axis remains on the central axis of the test channel. The clamping unit can be for example a clip, such as a switchable three-point clip, or a pair of pliers, such as a three-finger-like gripper, or a radial gripper. The clamping unit may have at least one mold element, preferably three mold elements that can be applied to the test piston. The mold elements offer preferably two opposed contact surfaces which are approximately in a longitudinal extension of each other. The contact surfaces can be applied depending on a piston to be clamped, at the first coupling region and the second coupling region. A frame is able to be formed, in particular bi-directionally, in the test piston axis direction. The clamping unit can be hydraulically or pneumatically actuated. As a further or another embodiment, these can also be configured in such a way that that an electromagnetically switchable bracket is available. For example, a lock can, in conjunction with the bracket, secure the connection between the drive unit and test piston as a centering clamping unit. The lock can be, for example, an electromagnetic lock, a pneumatic lock or a hydraulically actuatable lock. The fast assumption of a closed position or a release position enables access to the test or service piston in less than 10 seconds.

It is particularly advantageous if a proximity sensor or an approximation sensor is allocated to the bracket. The proximity sensor detects whether an object is in a spatial environment of the proximity sensor, which is able to be allocated to the test piston or the head of the test piston. The proximity sensor can provide a distance change determination, in particular a positional determination, and can be designed, in particular, as centering aid. The proximity sensor preferably works inductively, wherein a positional determination takes place in the active range of at least one magnetic field of the test flow machine. The proximity sensor allows particularly fast and accurate approximations to the test piston. It is also possible to use proximity sensors that operate mechanically, electromagnetically, especially visually, or thermally. The mold element can be equipped with a proximity sensor, for example. The movement of the piston can be implemented in a controlled manner and carried out quickly, so to speak.

According to a further favorable embodiment of a flow test machine, a path measurement device is provided. The piston position measurement device can be a path measurement device. A path measuring device collects or measures, in particular, a difference in the positions of the piston such as a test or a service piston by its gap or by using measuring technology for determining a gap by its absolute value. The path measurement device can advantageously interact with a test cylinder in a control. The path measurement device determines, at which point, in particular within the test channel, the test piston or service piston is located. It can also be said that the piston position measurement device or the path measurement device detects how far, for example, the test piston is still able to be inserted into the test channel to reach or to exceed a predetermined position. A travelled or passed path of the test piston or of the service piston is measured with the piston position measurement device. The path measurement device forwards a position associated with the test piston as a digital signal to a control unit, in particular of the flow test machine. The path measurement device provides, in other words, a position signal. The control unit processes the position signal to control, in particular, a holding element. For the holding element, depending on the configuration, different positions are provided. The holding element can be located on the test piston or on the service piston. The holding element can be located on the test weight, in particular the test weight body, and/or on a test weight receiver. In a further embodiment, the holding element can, however, also be located on the arm, in particular on an arm end. A holding element may, according to one aspect, comprise a physical form that is provided for the connection to, in other words the formation of, a holder. In a working region of the flow test machine, which can also be referred to as the test region, the elements of the test flow machine allocated to the holding element are able to be approximated by the drive unit. The position signal can serve as interlock for the closed position or the release position, particularly in an area of a test stretch, to ensure a standard measuring operating state.

The flow test machine can have a time control unit, which includes in particular a stopwatch. The time control unit can work as timer, for example as an electronic time control unit, such as through a microchip of the control unit, or as a timekeeper. The time control unit sets switching times in the course of a flow test. Switching times in the course of each step of the process can be determined. According to another aspect, the time control unit serves to monitor a cycle time. In other words, the time control unit detects the point in time at which the coupling or the holder is to be opened, and sets the point in time at which the actuating additional force on the test piston or service piston is to be switched on. In conjunction with the path measurement device, flow rates of a test mass are able to be measured by the time control unit.

Another beneficial component is a heating device in the flow test machine, such as an electric heater, in particular a resistance heating, for example with a heating wire, or an eddy current heating. The heating device enables a very even heating along the length of the test channel. Thus, it is possible to homogenize the fluidity in a pillar of the test mass. A first heating unit can be arranged around the test channel. A second heating unit can be arranged in the test piston or service piston. A nozzle with a heating device may also be provided as a modularly usable element.

The time control unit and the heating device can work together beneficially. The heating device preferably includes a temperature measurement device with a temperature sensor, in the manner of a digital thermometer. With the help of the temperature measurement unit, it is verifiable as to whether the test mass reaches a settable temperature, such as a melting point. The time control unit monitors a settable melting time. It is possible only to allow a next process step by the control unit when a release signal of the temperature measurement unit and a waiting time signal of the time control unit are present. The driving force, just as the weight force and/or the actuating additional force, is set in action via a signal to the coupling unit, for example. In other words, ideally a drive state will only be assumed if the flow test temperature, for example for a thermoplastic material, is achieved and the predetermined melting time is passed. In the drive state, a force of the drive unit and the weight force are parallel. Therefore, a driving force is provided in addition.

The drive unit may advantageously also generate a force which is directed contrary to the weight force, in particular when the drive unit is operating in a second operating state. A second operating state may be given, for example, when a measurement operating state is finished. In one aspect, a second operating state may be a drive state. The force in a second direction running contrary to the weight direction can be generated by means of a deflection device in the drive unit. The deflection device can, for example, be at least one switching valve. For example, a hydraulic or pneumatic change-over switching valve is suitable as a switching valve. The deflection device may also comprise a combination of several hydraulic and/or pneumatic switching valves. The switching valve may exist in a form of a 3/2-way valve. A first working connection is active when the drive unit is working in the same direction as the weight force. A second working connection is active when the drive unit is working against the weight force. The switching valve may cooperate with the test cylinder. A pressure medium can be introduced into a working space at one end of the test cylinder via a respective working connection located between the switching valve and the test cylinder. It is advantageous if the force starts in the second direction on the test weight. The force can be applied, for example, to a test weight body. This has inter alia the advantage that the test weight is able to be brought by the drive unit, in particular in a very short time, back into a position above the first position, in particular without the interaction with a user. If the bracket is in the release position, the test piston may be left in the achieved position or reached position. In this configuration state of the flow test machine in which the bracket is in a release position, the mass of the test weights can be safely and quickly removed.

Further, it is advantageous if a pressure control unit is provided. A proportional pressure control valve can, for example, function as the pressure control unit. A supply pressure can also be digitally limited via a control loop by means of a pressure gauge, such as a digital manometer. Due to the pressure control unit, the actuating additional force can be regulated. The actuating additional force is therefore at least proportional to a pressure force. It can also be said that the actuating additional force follows the set pressure. The actuating additional force can be adapted continuously to the fluidity of the test mass. An upper limit of the actuating additional force is determined from a supply pressure for the hydraulic and/or pneumatic components of the flow test machine. Preferably, the upper limit is chosen so that the test piston does not exceed a maximum speed. The pressure control unit is able to monitor compliance with an upper pressure limit. The pressure control unit collaborates advantageously with a control unit, in particular with control electronics. The pressure control unit and the control electronics are connected via an electronic control line. Regulation of the test piston speed is executable by the pressure control. A pressure increase causes—usually—an increase in the test piston speed, especially when the increase in pressure in the test material takes place phase-transition-free or especially if an increase in the test piston speed does not produce or reinforce any flow turbulences (e.g. purely laminar flow). The control unit and the pressure control unit can form a regulation for a pressure force, especially to a constant amount. The regulation may result in a constant test piston speed. It is also possible to obtain a constant test piston speed by regulating the pressure force.

A maximum pressure can be predefined, with which the test piston is able to be loaded by the drive unit. A pressure source can be a hydraulic pressure source, a pneumatic pressure source or an electrical or mechanical pressure source, each for pressure generation, providing a pressure force that is able to be applied to the test piston.

One of the second positions of the test piston may be present as a work area end position, which can also be referred to as an end position of a region for experiments. The end position of the region for experiments is located at a downstream side of the test channel or on an outflow side of the test channel. An opening on the outflow side of the test channel can be referred to as a nozzle or press-out nozzle. In other words, a limitation of the test channel is preferably a nozzle. The working range of the test piston terminates at the nozzle. The test piston cannot exceed the end position of the region for experiments because the nozzle, in particular a nozzle insert, defines a path of the test piston. In one aspect, it can also be said that the nozzle may be a constriction of the test channel, such as a bore with a smaller diameter than the test channel. The nozzle may also be designed as a nozzle insert of the test channel, so that a clogged nozzle is to be replaced quickly, if necessary. A removable, preferably ejectable or at least displaceable, modular nozzle insert facilitates the implementation of a cleaning process for the test channel. The nozzle has a minimum diameter, for example, an entrance diameter and an exit diameter, which are in particular spaced apart by a nozzle channel length. In an advantageous development, the opening is connected to a lock or to a cutter which, for example, includes a cutting wire. For example, the exit diameter can be covered in a lock position.

One of the first positions, a starting position, can be provided as a test area end position. The test area end position can also be described as a post-test area end position because the test area end position in particular marks a standardized minimum distance to the nozzle. In other words, a first position can be arranged between one end of the test stretch associated with the nozzle and the nozzle itself. The end position of the region for experiments is located outside the test stretch. The test piston passes, coming from the test stretch, a partial stretch of the test channel, which is also known as post-test area or as a test stretch annex. The test area end position can be considered as the end of the test stretch and as the beginning of the second partial stretch. The second partial stretch down to the end position of the region for experiments is shorter than 2 cm according to an advantageous embodiment. The end position of the region for experiments can be—in other words—also known as a rest position. Test material remaining in the test channel after a precise flow test is efficiently ejectable.

One of the first positions, preferably a first position of the test piston that is closest to the filling opening of the test channel, may also be referred to as the experiment start position. The test piston is located at the beginning of a flow test in the experiment start position, which is in particular a rest position after a compression of the test mass. A second position, which in particular resides or is shown preferably to be the position closest to the second positions in the test channel of the nozzle, may also be known as the experiment end position. At the end of the flow test, the test piston is located in the experiment end position. If only one test stretch is provided, the experiment end position and the test area end position can lie together.

A third position and a fourth position are provided between the experiment start position and the experiment end position according to an advantageous development. Due to the third and the fourth position, the test body can pass through without stopping at the positions. It can also be said that the third and the fourth position represent transitory positions or passage positions. This third position is a test start position. As soon as the test piston is in the test start position, the measuring process begins, in particular a first timing occurs. The fourth position is a test end position. In the test end position, the measurement process is finished, wherein in particular a second timing takes place. The test stretch, one of the partial stretches of the test channel, lies between the test start position and the test end position. The actuating additional force can be separated from the test piston before reaching the third position. The position of the test piston for the separation is a second position, an end drive position spaced from the third position. In transitory, continuous motion of the test piston, a relaxation of the test mass takes place at a lower test piston speed up to the third position. The test piston speed that is higher before reaching the second position allows a faster output of a flow of test material. Thus, a faster cycle time in the flow test is possible. In other words, the positions are respective, in particular imaginary points along the test channel, which have significance for the execution of the test, such as a change of state in the flow test machine, such as a timing position, such as a position accompanied by a force or other load change.

The test stretch can have, depending on the material to be tested, for example, a length of between 15 mm (millimeters) to 100 mm. Preferably, lengths between 6 mm and 26 mm are provided. At low expected melt volume flow rates, or at high viscosity, shorter test stretches are advantageous; at high expected melt volume flow rates, longer test stretches are advantageous to obtain good measurement results.

The direction of the actuating additional force is, at least in one of the operating states, equal to a direction of the weight force, which may be placed on the test piston in one of its first positions. The predeterminable and adjustable actuating additional force is reversible in direction, at least in respect of its absolute value. The reversal of the force causes a deceleration of the test piston. It is possible to increase the actuating additional power, so that the test piston comes to rest by compensating for the weight amount. The press-out path is, in one configuration, the partial stretch of the test channel, which the test piston passes through down to the experiment end position after passing through the fourth position, so after the end of the timing during the flow test. On the press-out path, the test channel is at least partly cleared by an advance of the test piston. A slow approach to the second position takes place through a deceleration before one end of the press-out path. The test piston comes to a standstill, for example, targetedly at the end of the work area. Pressure peaks which may have negative effects on flow tests or on the flow test machine are avoided. No safety distance with remaining test material on the path of the test piston to the nozzle has to be adhered to. It is also possible to make a partial compensation of the weight force, coming in particular from a mass of the test piston, with the actuating additional force during flow tests of particularly low-viscosity fluids.

The press-out path is allocated to a, in particular second, press-out step, such as a cleaning step, of the measurement method for a flow test, thus a melt viscosity test. According to a second aspect, a press-out path can also be allocated to a measurement preparation step, which thus depicts a first press-out step.

The actuating additional force from the test cylinder is equal to the weight force direction until the test piston has arrived at a force turning point. From the force turning point, a force running counter to the weight force of the test weight acts on the test piston. Due to a piston position measurement device, which can be called also piston position measurement device, the position of the test piston is recognizable in which the force turning point is located. In other words, a force direction is able to be reversed in the press-out step, in particular by means of controlling the test cylinder. A force turning point is beneficially located in an area of the test channel in which the pressure surface of the test piston from the nozzle is arranged between 0.1 mm and 20 mm away. The path of a piston may be ascertained through the piston position measurement device.

In a particularly advantageous embodiment of the flow test machine, an arm is provided. The arm can be arranged between the coupling and the drive unit. In an advantageous embodiment, the arm is inserted between the bracket and the test cylinder, with which the bracket can be positioned particularly well with regard to the test cylinder. The arm can extend at least in areas in a radial direction with regard to the test cylinder. The arm is able to be moved by the drive unit. The arm is designed such that, in particular dimensioned to such an extent, that it can receive or bear the test weight, in particular a maximum test weight. In other words, the arm is designed in order to bear the test weight. The arm has two arm ends. An opening is located at a first arm end. The opening can be a, in particular cylindrical, continuous recess. The opening is able to be arranged around the test piston, more exactly around the test piston head. According to another aspect, the arm is able to be positioned along the test piston, in particular along an area of the test piston which is located outside of the test channel, on a conceived plane. The test piston is able to be arranged without contact in the opening of the arm. It can also be said that the opening extends from a test channel side of the arm to a test weight side of the arm. An upper side of the first arm end can have a contact area and preferably a centering area for a test weight, in particular for a first test weight body. At least one holding area for the test piston head can be present on an underside, so a side facing towards the test channel, of the first arm end. The bracket can be arranged in the holding area. A configuration with is spatially particularly favorable is present if the arm has an actuator, using which the at least two positions of the bracket are able to be switched. The holding area can—in an advantageous, constructive design—be formed as a part of the bracket, and in particular can offer a supporting mount for the bracket.

The arm is preferably mounted rotatably. An ability to pivot of the arm is advantageous, at least in an end position, in particular an end position of the test cylinder or of the test piston, such as the experiment start position, so the position at the beginning of the experiment, and/or the experiment end position. During the test, the arm is not able to pivot. A pivot joint of the arm is preferably able to be set in order to ensure a straight-line guidance of the arm by the drive unit. The ability to pivot is present in particular in a plane which extends preferably perpendicularly with regard to the direction of the weight force. The pivotable arm facilitates the implementation of maintenance work, such as a manual access to the test piston for a removal of the test piston or such as during a filling of the test channel with test material. It may be emphasized that the test weight is able to be provided more quickly. With the aid of the arm, advantageously a first test weight can be replaced by a second test weight. Test weight bodies can be present in a test weight magazine. A test weight body of the test weight is able to be deposited in the test weight magazine or a test weight body is able to be received from the test weight magazine by means of the arm, in particular is able to be added to the already present test weight which can be arranged on the test piston.

Preferably, a second end of the arm, a second arm end, is connected to the drive unit. The connection can occur via a pivot joint. The second arm end can be rotatable in an angle range around an axis. It is possible to provide the ability to rotate of the arm using the drive unit, for example by means of a stepper motor.

According to a further advantageous embodiment, at least one stop is present on the drive unit. The stop can be realized by an end contact switch. The stop can, for example, be allocated to the second end of the arm. The stop offers a position determination of the arm, in particular of the opening of the arm, with regard to the test channel. The stop can also enable a position monitoring. According to one aspect, the stop limits an ability to rotate of the arm. According to a further aspect, the stop can be allocated to a second position. For example, the stop can be allocated to an end position, such as the end position of the region for experiments or the experiment end position, in other words to the test piston or also to the test cylinder. Preferably, the stop works as a switch of the drive unit in order to ensure a precise test procedure. If the test piston is located in the end position, e.g. of the control unit, the bracket, in particular an actuator of the bracket, is able to be switched into the release position. The test piston is able to be uncoupled from the drive unit in the stop position.

It is possible to provide an anti-rotation stop as a first stop. The anti-rotation stop preferably comprises a stop switch which is connected to a joint determination device. The first stop allows the switching of a drive direction of the drive unit in the direction of the weight force. An end position stop can be provided as a second stop. The second stop can be implemented as one, preferably two, piston position extreme values of the piston position measurement device or of the path measurement device which are held by the control unit. The second stop blocks the drive direction of the drive unit, in particular in the direction of the weight force.

For the implementation of flow tests for the melt viscosity test, it has proven to be advantageous if a movement direction of the test piston, in particular originating from the first position, is maintained. The movement direction remains constant until a stop is reached. As an alternative, the movement direction can also remain unchanged until the test piston is located in an end position. The end position can, for example, be the end position of the region for experiments or the experiment end position. The movement direction is supported by the actuating additional force. An acceleration acts on the test piston. The acceleration can additionally occur in addition to gravitation.

In particular, in connection to the accelerated movement, the test piston can be decelerated by the actuating additional force. The deceleration of the test piston can be initiated in that the drive unit is switched over. With the aid of a movement element of the drive unit, a shifting of a drive direction can be implemented, in particular maintaining the movement direction. In other words, also during the deceleration, at least during a fraction of a deceleration time, test material still leaves the test channel through a nozzle.

The actuating additional force preferably has a constant amount in a measurement operational state. During a press-out step it is possible to change a force direction of the actuating additional force. A reversed force direction is provided as a changed force direction. The change can occur steadily by changing the amount of the additional force. The additional force acts on the piston, advantageously on the test piston, in order to obtain a piston movement which is as even as possible. The additional force can also, for example, be applied to the cleaning piston, wherein during a press-out step, a reverse of the force direction is possible in particular to intercept the piston in an end position area. The force direction of the actuating additional force is the same as the direction of the weight force, until a force turning point is reached at which the actuating additional force on the piston experiences a change. In an area around the force turning point, the actuating additional force direction is opposed to the weight force direction. A change of the movement, in particular in the sense of a movement direction, results. The reaching of a force turning point is advantageously able to be checked with a piston position measurement device. For example, the test piston for a turn in the direction of the actuating additional force is provided at the force turning point. Thereby it is ensured that the force direction is correctly set in a test method or also in a cleaning step.

If the measurement preparation step is ended, the measurement step is initiated. A connection between the test piston and a drive unit which serves for a transfer of the actuating additional force is opened. Preferably, after a deactivation of the additional force, the frictional force is separated in order to obtain a movement which is as free as possible. The separation is advantageously executed by means of a coupling in order to prevent force peaks. After the separation, a relaxation time can be provided before the beginning of the measurement step. The relaxation time is a time of free movement of the test piston under the test weight. The relaxation time is measured such that a uniform test piston movement is achieved. In other words, the test mass, loaded by the test weight, can relax. The relaxation time can also be used advantageously to wait for a heat flow in a test space. A test temperature profile of the area of the test space which is allocated to the test channel, in particular a temperature profile in the test mass provided for the measurement which was moved into proximity to the nozzle in the measurement preparation step can be spatially homogenized. The aspect of the homogenization implies that a temperature is present to be spatially homogenous in the test mass, wherein the temperature is preferably the same as a nozzle temperature. The homogenization can occur under constant supply of heat from a heating device. After the expiry of the relaxation time, the test conditions are particularly reliable. A time recording represents the beginning of the measurement step. During the measuring, a test weight transports the test mass, for example through the nozzle. A weight force drives the test mass via the test piston. The measurement step is ended by a second time recording. It is possible to detect intermediate times in order to analyze the measurement step following temporal developments, for example in order to recognize chemical changes of the test mass.

At least one material property of the test mass is determined from a movement of the test piston. The evaluation of data which is obtained from a measurement step occurs in a calculation unit. The calculation unit can be a part of the flow test machine. It is advantageous if the calculation unit interacts with the control unit of the test machine in order to come to results quickly. The measurement step can comprise a path-time measurement. The path is a path stretch of the test channel which contains a volume of the test mass, such as a test volume. The test volume is pressed in a time interval, for example by the nozzle. A test mass section can also be clipped which comprises the test mass of the measurement step. The escaping test mass of the test material can be ascertained or determined by weighing, said test mass in particular not having to be assigned to the press-out step, so also not to the measurement preparation step. A weighing device can be a part of the flow test machine. The weighing device preferably interacts with the calculation unit in order to come to results even more quickly. Therefore, at least one material property, such as viscosity of the test mass or a flow speed, for example the melt mass flow rate or the melt volume flow rate, in particular in the case of a constant temperature, can be determined. The melt mass flow rate and the melt volume flow rate serve as a measure of the viscosity of a melt of a plastic. Conclusions can be drawn as to the average number of monomer units in a polymer molecule of a test material.

The cleaning method advantageously has at least one partial step, preferably a sequence of partial steps. Through a use of partial steps, a cycle for a flow test can be structured in a particularly favorable and time efficient manner. One or more of the following, in particular further, partial steps can be provided.

In one partial step, for example a first partial step, the decoupling of the drive unit by an actuator occurs. The drive unit and the test piston are separated from each other. The separation occurs by control of the actuator.

Another partial step, for example a second partial step, comprises the removal of the test piston from the test channel. The removal can occur automatically by the drive unit or manually by the machine operator.

Another partial step, for example a third partial step, comprises the coupling of the cleaning piston to the drive unit. In particular, an alignment of the cleaning piston with regard to a central axis of the test channel occurs during coupling.

Another, for example fourth, partial step comprises the retraction of the cleaning piston into the test channel. The drive unit moves the cleaning piston into the test channel, preferable until the nozzle is reached.

Another, for example fifth, partial step comprises the extraction of the cleaning piston from the test channel. The extraction occurs, for example, by means of the drive unit. It is also possible to implement the extraction at least on a partial stretch, in particular as a manual removal. The extraction can, for example, comprise the press-out-side emission of a cleaning agent, such as a cleaning plug or cleaning cloth, from the test channel.

Another, for example sixth, partial step comprises the decoupling of the cleaning piston from the drive unit. The decoupling can be initiated via an actuator.

Another, for example seventh, partial step comprises the coupling of the test piston to the drive unit. The coupling is able to be executed, for example, by an actuator.

Another, for example eighth, partial step comprises the driving of the test piston in the test channel. The driving can occur by means of a drive unit. Preferably, the test piston is driven up to a nozzle.

A further partial step, for example a partial step which is able to be executed between the seventh step and the eighth step, comprises the filling of the test channel with a test material, in particular with a test mass, which was pretreated, preferably for cleaning, for example in a crusher, a washing device, a mixing device or an desiccator. It is also possible, for example, to fill the test channel with a cleaning granulate or a cleaning fluid between partial steps.

A piston, such as a test piston or a service piston, can be received in an actuating manner from a piston magazine or deposited in an actuating manner in the piston magazine. In particular, the piston can be moved between the test channel and the piston magazine on an arm with the drive unit. The cleaning method can also comprise a sequence of partial steps to be repeated.

During the implementation of a cleaning step which is connected to the measurement method, it is advantageous if the temperature is maintained at a predetermined temperature value. A temperature control on the flow test machine ensures that a flow temperature of the test material is present. The temperature control is, for example, able to be executed by at least one temperature sensor, in particular at the test channel. The heat capacity of the flow test machine, in particular a test channel cylinder, is preferably sufficient such that the test mass remains fluid during a test time.

It is favorable for an at least partially automatic operation of a flow test machine if a control unit is provided. The control unit can, for example, control a test cylinder or also an actuator of a bracket. The control unit can also lead an arm to a test weight magazine or to a piston magazine. It is particularly advantageous if the control unit meters the actuating additional force. An actuating additional force, a cleaning force, is applied to the cleaning piston by the control unit. It is, for example, possible, to increase the actuating additional force exerted on the cleaning piston using the control unit at a movement obstacle present due to an impurity in the test channel, in particular in the case of a recognized movement obstacle, until the movement obstacle is eliminated. According to another aspect of the control unit, the cleaning piston which is subject to, for example, a force of a test weight or of a cleaning weight, so a cleaning weight force, can be decelerated in particular before reaching a nozzle. A control of the actuating additional force by the control unit for application on the test piston or the compression piston is also particularly advantageous. A control of the actuating additional force occurs sequentially according to requirement. Within the individual steps of the cleaning method, in other words for the execution of a cleaning step or of a partial step, the actuating additional force is able to be controlled and is in particular able to be varied. For example, an additional force which is lower in amount can be applied to the cleaning piston during retraction into the test channel than during extraction from the test channel.

The test channel is particularly dimensionally stable if it is arranged in a cylindrical body. Pressure forces in the test cylinder can therefore only cause a radially symmetrical deformation which is low even in the case of a low mass of the body such that test results remain unimpaired. The test channel is preferably arranged to be unrelenting with regard to a drive unit. The filling opening can have a conical channel, with which a quick filling of the test channel is favored and in particular the insertion of a piston is facilitated. Preferably a switchable directional channel is provided between the nozzle and the weighing device which has a preferably lotus-like, repellant surface quality. In a switch position of the directional channel, sections of the test material which resulted due to the press-out step are supplied to a collecting tank. In a second switch position, at least one section of the test mass is supplied to the weighing device. Therefore, particularly accurate weighing of the test mass can be implemented without loss of time.

A flow test machine according to the invention is also able to be used for tests for material testing which represents a further development, in particular based on existing standards. Due to the numerous variants and combination possibilities, advantageous embodiments of the described flow test machine as well as test variants result, in particular due to their control, which are considered below or as a further development of the standards. For example, test masses can be pressed out by exchangeable nozzles with variable force profiles. From (individual) test to (individual) test, the material properties can be determined little by little more precisely. Error influences are, in particular with the aid of the control unit, able to be removed and eliminated.

The previously depicted combinations and exemplary embodiments can also be considered in numerous further connections and combinations.

BRIEF DESCRIPTION OF THE FIGURES

The present invention can be understood better still if reference is made to the accompanying figures which described, by way of example, particularly advantageous embodiment possibilities without limiting the present invention to these, wherein.

DETAILED DESCRIPTION OF THE FIGURES

Figure 1:
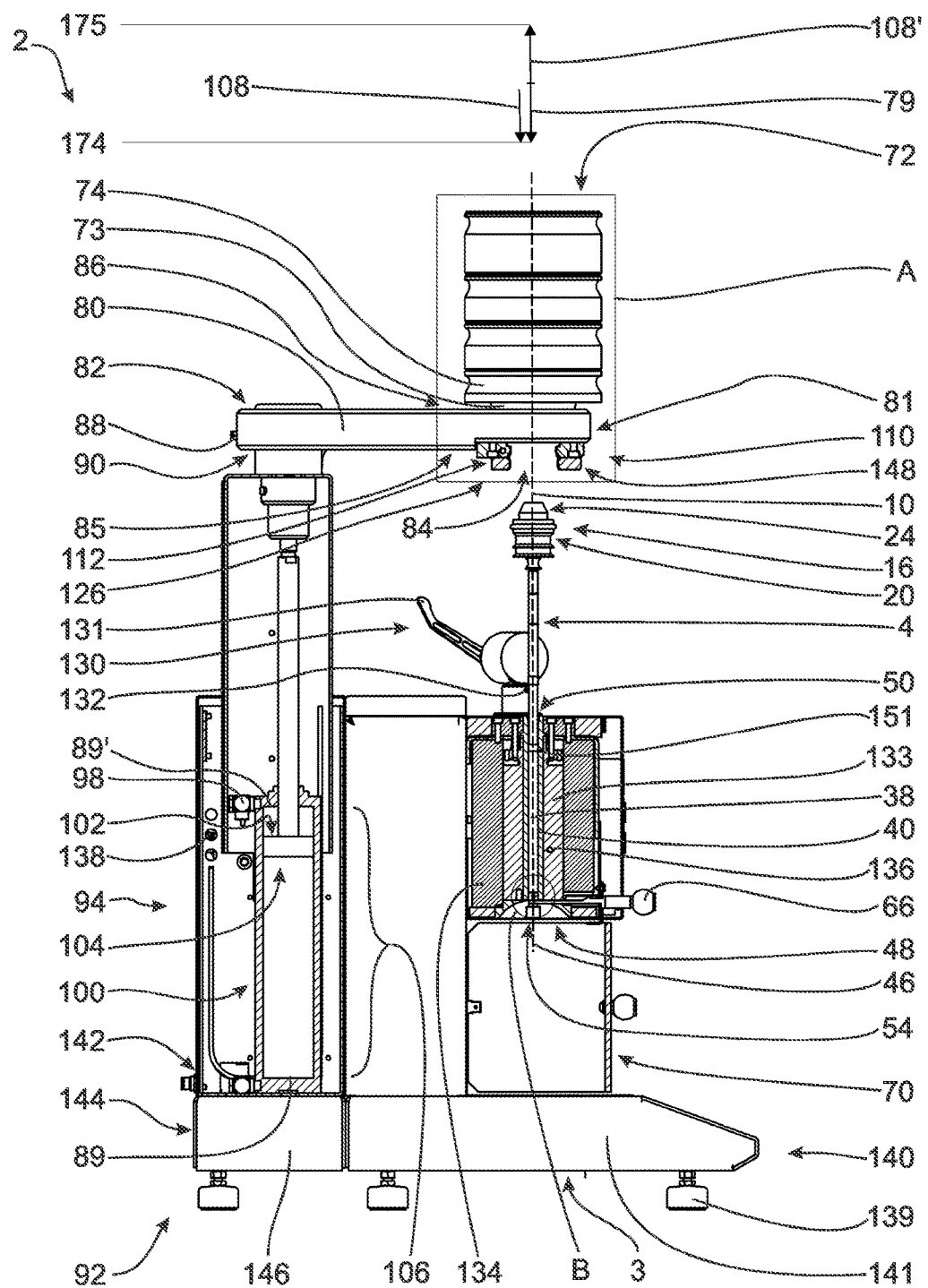
FIG. 1 shows a side view of a flow test machine.
Figure 3:
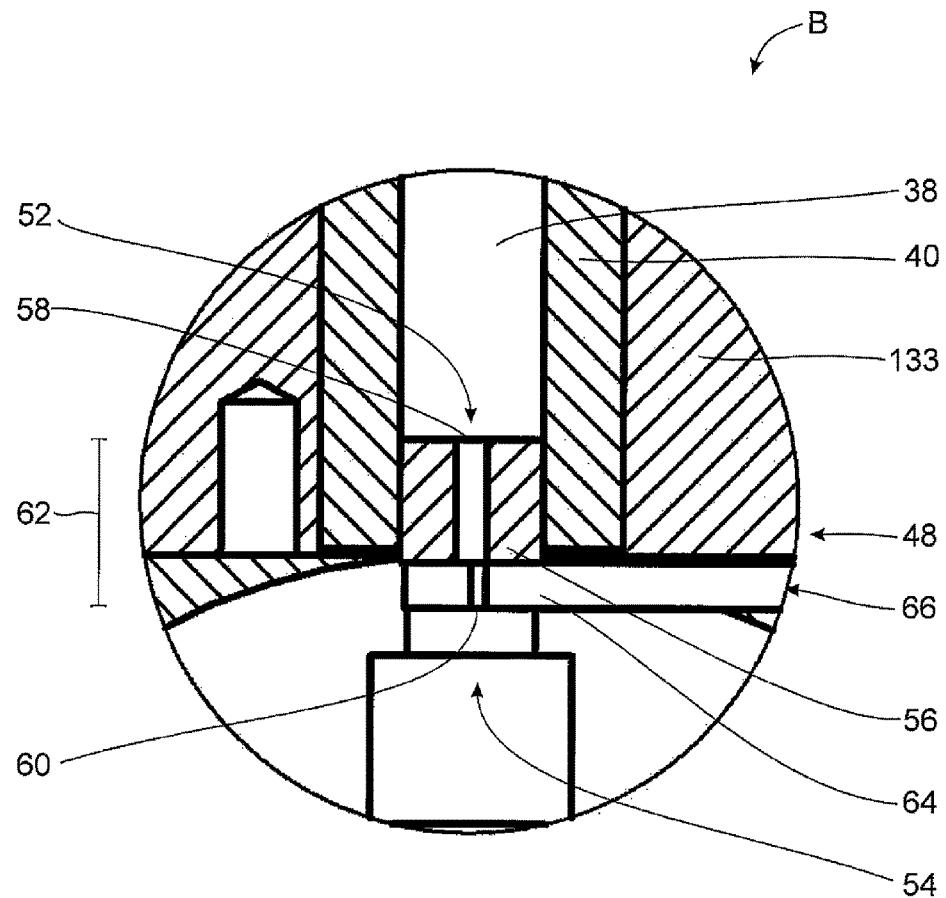
FIG. 3 shows an enlarged cut-out from FIG. 1, which comprises the nozzle on the downstream side of the test channel.
Figure 4:
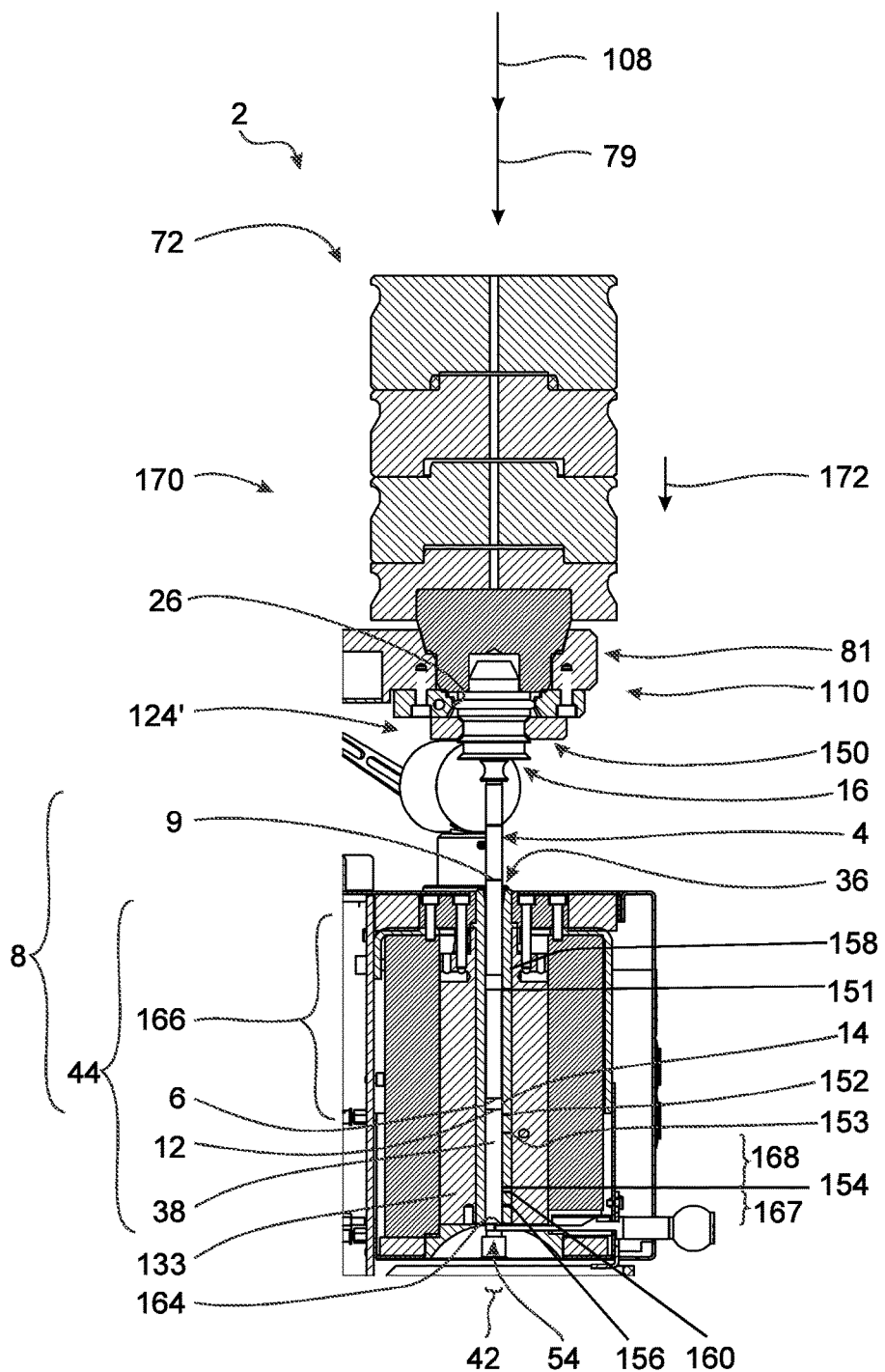
FIG. 4 shows an enlarged cut-out from FIG. 1, in a cross-sectional depiction, with the test weight and downstream side of the test channel in a measurement preparation step.
Figure 5:
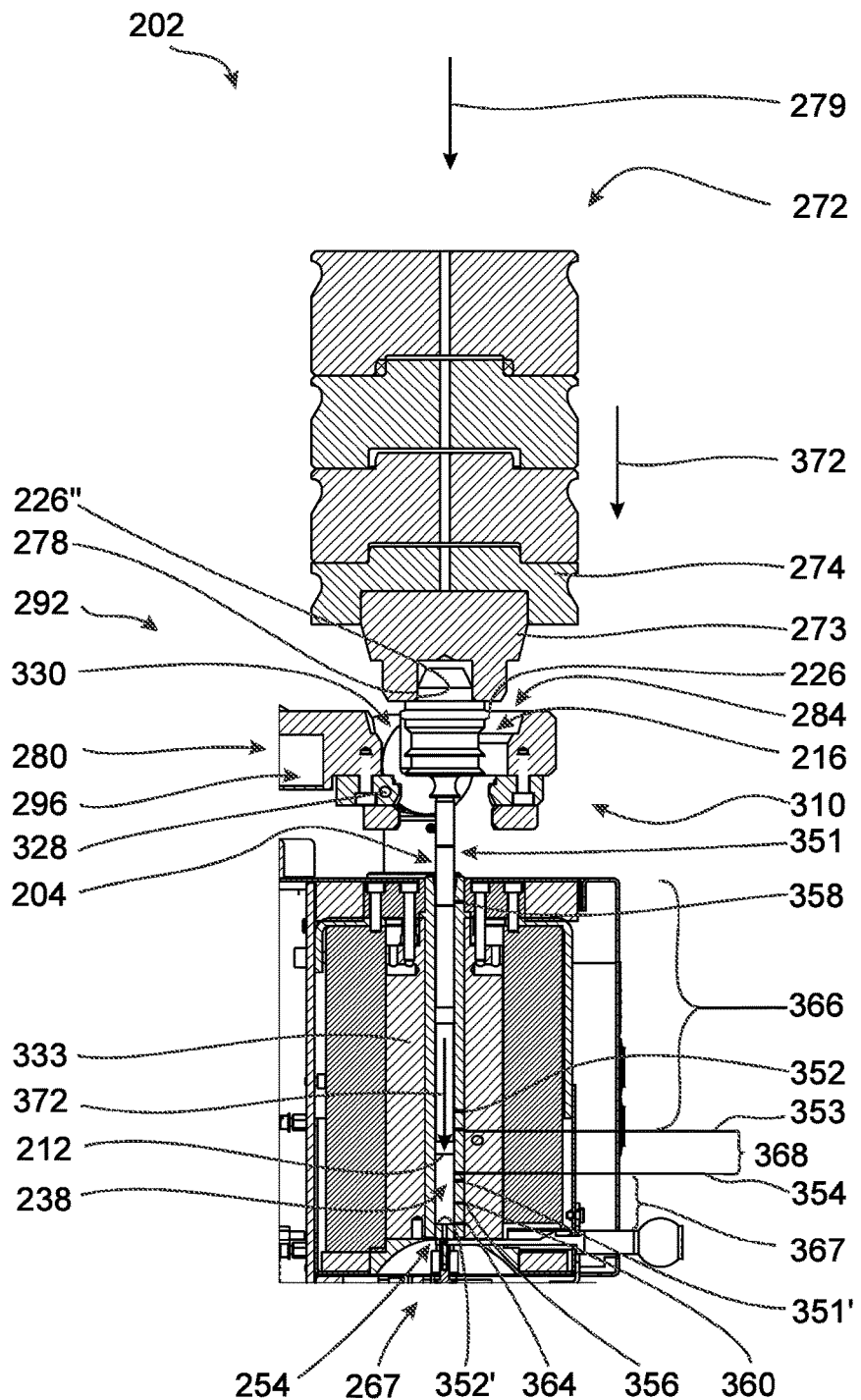
FIG. 5 shows a further embodiment of a flow test machine, depicted in a cross-sectional view similar to FIG. 4 with the flow test machine in a measurement step.
Figure 6:
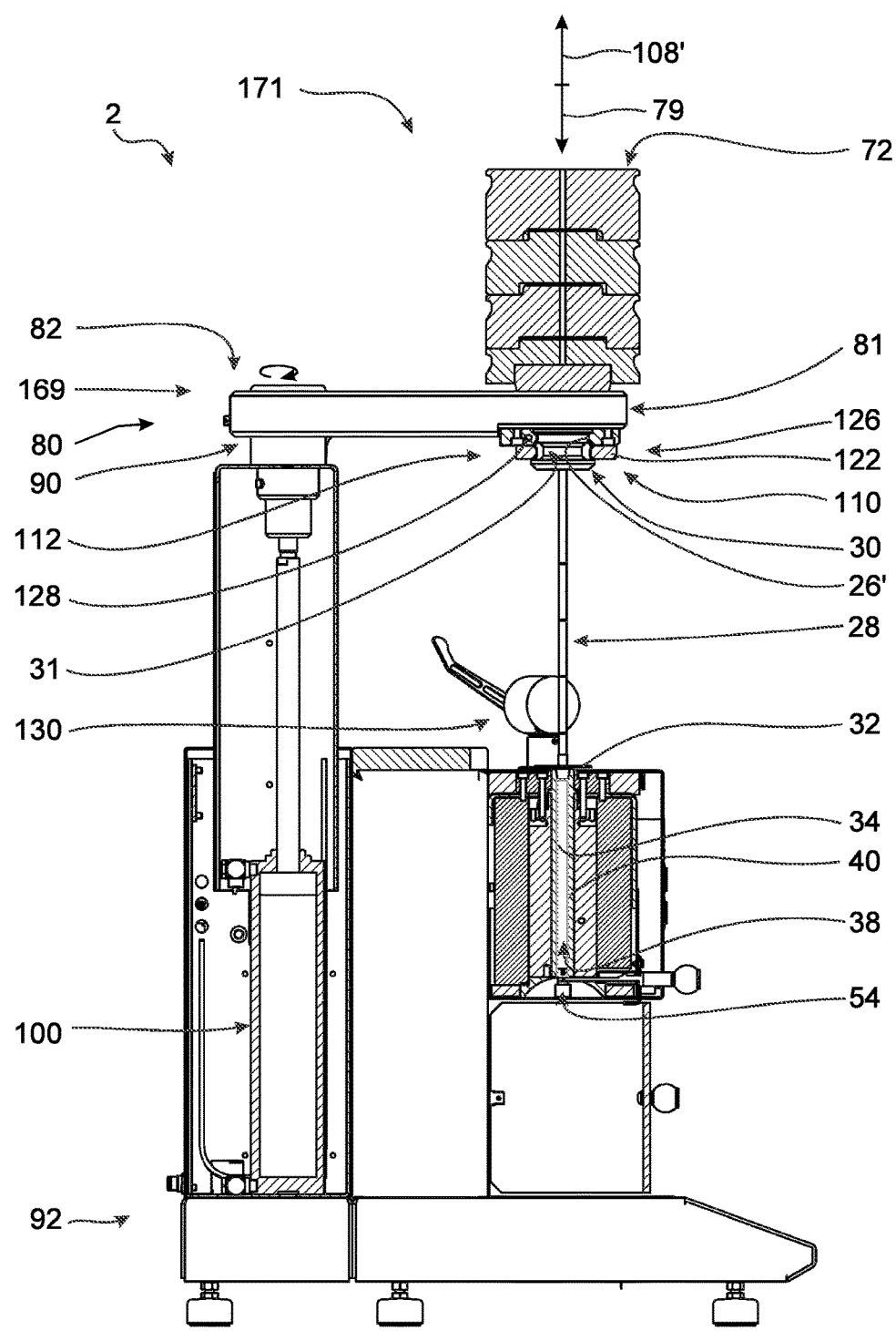
FIG. 6 shows the flow test machine from FIG. 1 with a cleaning piston.
Figure 7:
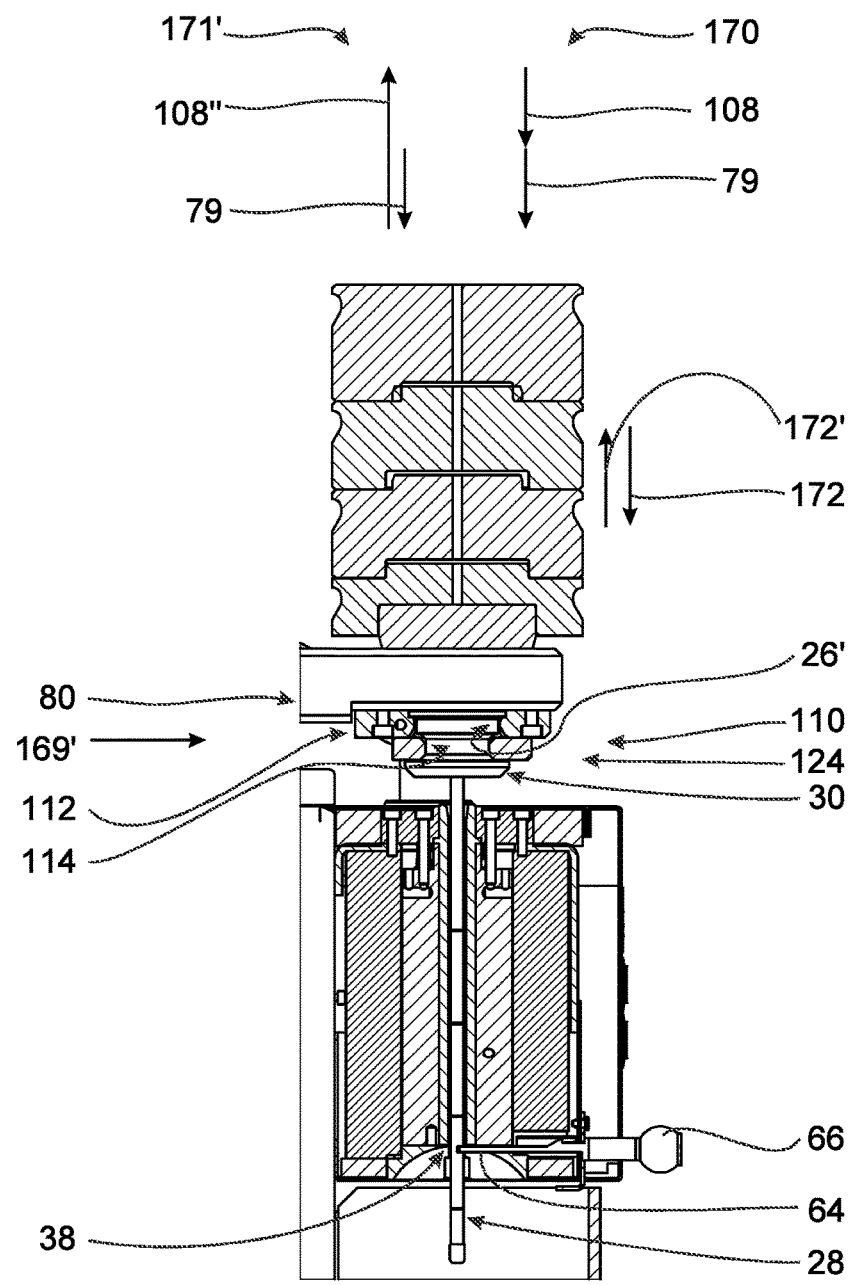
FIG. 7 shows the cut-out according to FIG. 4 of the flow test machine having the cleaning piston from FIG. 6 in a cleaning method having a cleaning piston which is slid through the test channel.

FIG. 1 shows a side view of a flow test machine 2 in a schematic representation, in which individual components are shown in cross-sectional view. The cut-out portion A is shown enlarged in FIG. 2 and the cutout portion B is shown in FIG. 3 enlarged. Other views of the flow test machine 2 are shown in FIG. 4, FIG. 6 and FIG. 7. FIG. 5 refers to, among other things, optional further developments of a flow test machine 202. The numerals of reference from reference numeral 2 to reference numeral 199 refer to one of the first examples of flow test machine 2 and the method of the invention, which are exemplified schematically in FIG. 8. The further explanations using the numerals greater than 199 can also be read in or transferred to, by way of example, the first exemplary embodiment, in particular, by subtracting 200 from the reference numerals. FIGS. 1 to 8 are therefore discussed together in the following.

The flow test machine 2 shown in FIG. 1 has a removable test piston 4 with a test piston head 16, which extends along the test piston axis 10. The test piston 4 is plugged on the filling side into the filling opening 50 of the test channel 38, wherein the test channel 38 created by the or is limited laterally by the test channel cylinder 40. The test piston axis 10 connects to central axis 46 which is fixed in the flow test machine 2. It can also be said that the test piston axis 10 and central axis 46 overlap in the working position of the test piston 4. The test piston 4 is located in a starting position 151. In the first switching position 148, the coupling unit 110 is open and ready for the centered fixing of test piston head 16. The coupling unit 110 is located at the first arm end 81 of the arm 80. The bracket 112 is arranged on the test channel side 85 of the arm 80. In the release position 126 of the bracket 112, the test piston head 16, in particular the support region 24 and the first coupling region 20, can be inserted into the bracket 112. The arm 80 is a part of the drive unit 92. The arm 80 can move along the test piston axis 10 towards the test piston head 16, in particular until the support region 24 adjoins the test weight absorber 73. The test weight absorber 73 lies on the test weight side 86 of the first arm end 81. The test weight absorber 73 is accessible through an opening 84 of the first arm end 81. Further test weight bodies, such as the test weight body 74, are supported on the test weight absorber 73. The test weight absorber 73 and possibly further test weight bodies such as the test weight body 74 together form the (entire or summary) test weight 72. The second end 82 of the arm 80, equipped with an anti-rotation stop 88 which has a stop sensor sit on the fixable pivot joint 90. The arm 80 and the supported test weight 72 are aligned along the central axis 46 at the stop 88.

The path measurement device 130, which has a measurement lever 131 allocated to the arm 80 and a stretch sensor 132 allocated to the test piston 4, is arranged (as seen in FIG. 1) to be laterally offset from the filling opening 50 of the test channel 38. The stretch sensor 132 is used to measure partial stretches of the movement of test piston 4. The drive unit 92 is connected, via the control unit 140, to the path measurement device 130, electronically via control lines (hidden in the FIG. 1).

The drive unit 92 includes a first actuator 94 having a test cylinder 100. In the test cylinder 100, a first control side 102 and a second control side 104 are able to be loaded with a means of pressure such as compressed air. Pressurization on the first control side 102 causes a first force direction 174. Pressurization on the second control side 104 causes a second force direction 175, which is opposed vectorially to the first force direction 174. The first force direction 174 and the second force direction 175 are parallel to the weight force 79 of the test weight 72. In the arrangement of the test weight 72 shown in FIG. 1, an actuating additional force 108' from the drive unit 92 is present, which is equal in magnitude to the weight force 79, and the direction of which opposes the weight force 79 by pressurization of the drive unit 92 on the control side 104. Because of the equality of weight force 79 and the additional force 108' the arm 80 remains motionless. By means of a deflecting device 142, which comprises a switching valve 144 in a switching valve case 146, it is possible, to switch between the pressurization on the first control side 102 and the pressurization on the second control side 104. Therefore, an actuating additional force 108 can be quantitatively supplied to the test piston 4, which has vectorially the same direction 174 as the weight force 79. The weight 79 is additive reinforced in amount, so without losses due to angled force components. However, a lowering of the arm 80 to the test piston head 16 can also take place under the effect of the test weight 72 in that the actuating additional force 108' is quantitatively or by absolute value reduced by reduction of an average test pressure via the pressure control unit 138. A lifting or lowering of the arm 80 to be executed by the drive unit 92 can be executed in precise increments, controlled via the control unit 140, with the speed control 98. A stop 89, 89' limits the movement of the drive unit 92 along the central axis 46 on a possible drive path 106. A time control unit 141 in a base 3 of the flow test machine 2 is able to be used both in measurement preparation steps as well as in measuring steps and cleaning steps, for example to coordinate movements of the drive unit 92 and execute them in conjunction with the control unit 140. The control unit 140 forms the base 3 of the flow test machine 2. The base 3 has a plurality of adjustable feet such as the adjustable foot 139, using which a vertical alignment of the central axis 46 of the test channel 38 is possible. The test channel 38 is embedded in a heater 133. The heater 133 is covered by a thermal insulating body 134.

The nozzle 54 which connects the test channel 38 to the press-out material chamber 70 is located on the outflow side 48 of the test channel 38. The nozzle slide 66 is located on a plane with the nozzle 54, with which the nozzle 54 is able to be closed. The nozzle slide 66 can also be used as a cutter for the test mass. The press-out material chamber 70 with separating door, for example, for weighing or for emptying, is removable from the flow test machine 2. It protects the pressed-out test mass from impurities such as water vapor, from the environment, which can lead to errors during weighing. Accidental skin contact with the often hot pressed-out test mass is prevented. The control unit 140 operates, among other things, as a temperature measurement unit and is connected to a temperature sensor 136 and to the heater 133. The temperature sensor 136 is located near the test channel cylinder 40. The control unit 140 can adjust the temperature of a test mass (not shown) contained in the test channel 38 to a stable value using the heater 133. The test channel cylinder 40 has a thermal conductivity of at least 15 watts/(meter*Kelvin). The heat can be evenly distributed over the test channel cylinder 40. Due to the arrangement of the temperature sensor 136 separately to the test channel cylinder 40, the test channel cylinder 40 can be replaced quickly if, for example wear should be recognizable.

Figure 2:
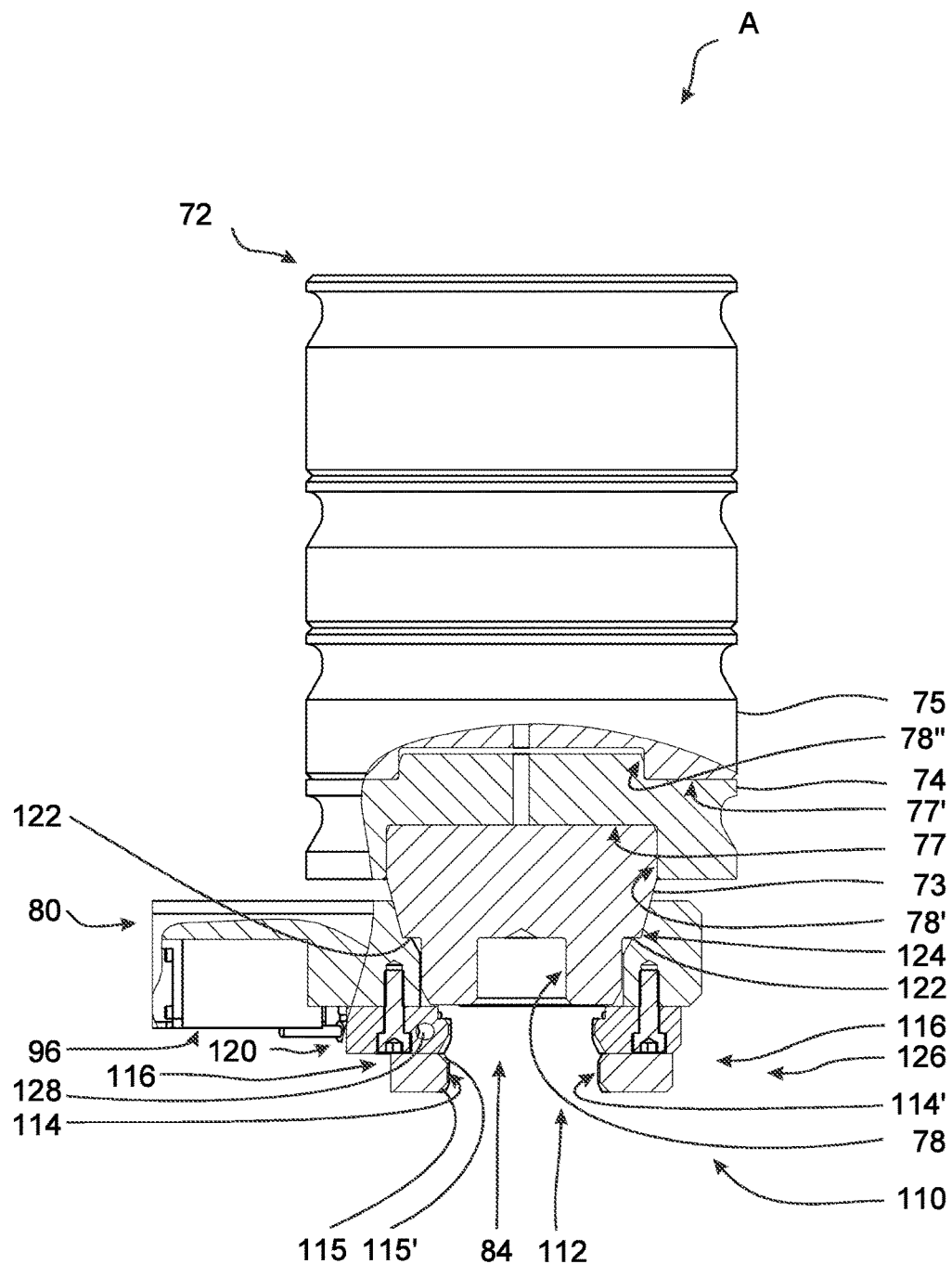
FIG. 2 shows an enlarged cut-out from FIG. 1 which comprises the arm end and the test weight.

The cut-out A, taken from FIG. 1, which is more clearly represented in FIG. 2, shows the test weight 72 of the flow test machine 2 arranged on the arm 80 (shown in sections). In the area shown in cross-sectional view in FIG. 2, the coupling unit 110 is shown, which is able to be actuated by a second actuator 96. The second actuator 96 can close, set and open a lock 120 which can be actuated pneumatically. Here, the clamping unit 116 touches a piston head (not shown in FIG. 2, for example, see FIG. 1). The clamping unit 116, which is part of the bracket 112, operates in a centering manner relative to the central axis 46 (see FIG. 1). The clamping unit is 116—in FIG. 2—shown in a release position 126. The clamping unit 116 includes the mold elements 114, 114'. Each mold element 114, 114' in each case has the contact surfaces facing towards the opening 84, such as the contact surfaces 115, 115'. The contact surfaces 115, 115' formed to fit to a coupling area of a piston head (see, for example, coupling area 20 in FIG. 1). The centering region 78 can receive the support area of a piston head 16 (see i.e. FIG. 1). A proximity sensor 128 is installed on a side of the arm 80 facing the opening 84. As can be seen in conjunction with FIG. 1, the proximity sensor 128 (shown in FIG. 2) is connected to the first actuator 94 and the second actuator 96 by control lines via the control unit 140. The proximity to a piston head 16 is recognized inductively by the proximity sensor 128. A signal output of the proximity sensor 128 is used to control the second actuator 96 when the coupling 110 is brought into a closed position, such as the closed position 124' in FIG. 4. The test weight absorber 73 sits in the opening 84 and, with a holding element 122, assumes a closed position 124 relative to the arm 80. Further test weight bodies, such as the test weight body 74 and the test weight body 75 are stackable on the test weight absorber 73. If the test weight absorber 73 is considered as a first test weight body of the test weight 72, then the second test weight body 74 is supported in the support area 77 between the test weight absorber 73 and test weight body 74. The second test weight body 74 is centered to the control unit 140 with regard to the test weight absorber 73. The third test weight body 75 is supported on the second test weight body 74 in its support region 77'. The third test weight body 75 is centered in a centering region 78" with respect to the second test weight body 74. The focal points (not shown) of all test weight bodies, such as the test weight bodies 73, 74 and 75, therefore lie along a straight line, which is aligned on the central axis 46, entered in FIG. 1. The test weight 72 is thus able to be placed stably on the test piston 4, which is shown in FIG. 1.

In the enlarged cut-out area B, which is depicted in FIG. 3, among other things, nozzle 54 arranged on the outflow side 48 of the test channel 38 of flow test machine 2 (see FIG. 1) is shown. The nozzle 54 extends over a nozzle channel length 62 and has, at the exit opening 52 of the test channel 38, a nozzle inlet diameter 58, which is greater than the nozzle outlet diameter 60. The nozzle outlet diameter 60 is located in a nozzle holder 64. The nozzle 54 thus comprises two components, a nozzle insert 56 with the nozzle inlet diameter 58 and the nozzle holder 64. The nozzle holder 64 holds the nozzle insert 56, having the nozzle inlet diameter 58, in the test channel 38. The nozzle holder 56 is operable with the nozzle slide 66 and can be swiveled to the side. The nozzle insert 56 is removable inside the test channel cylinder 40. The heater 133 extends on the test channel cylinder 40 into the region of the nozzle 54, so that the nozzle outlet opening 60 is also maintained at temperature required for a flow test.

The area of the flow test machine 2, which is shown in FIG. 4, represents a first operating status 170. The actuating additional force 108 acts 81 on the first arm end 81 in the same direction as the weight force 79 of the test weight 72. The test piston 4 follows a movement direction 172 in the test channel 38, which is in the same direction as the additional force 108. The test weight 72 rests on the first arm end 81. The coupling unit 110 is located under the test weight 72 in a closed position 124'. A second switch position 150 of the coupling unit 110 is provided in which the piston head 16 firmly sits on the first arm end 81. A position of the test piston head 16 is laterally, in other words, in an auxiliary plane directed at a right angle to the weight force, limited by the centering region 26, arranged in the coupling unit 110. The centering region 26 improves a reproducibility of an allocation or alignment of the test piston 4 to the test channel 38. The closed position 124' is able to be assumed precisely. The test piston 4 crosses the test space 36, which can be seen in FIG. 4 using the drive unit 92, shown in FIG. 1. The test piston length 8 is the distance between the test piston head 16 and a pressing surface 12. The test piston 4 has length markings, such as the length marking 9, which are able to be used, for example, as calibration aids for a path movement. The pressing surface 12 acts on test material (not shown) that exists in the test channel 38. The test channel 38 has a channel length 44. The channel diameter of 42 is greater than the piston diameter 6 and in particular greater than the press-out nozzle 54. The channel diameter 42 has a value between 8 mm and 10 mm. A sealing area joins the pressing surface 12, which covers the piston diameter, along the test piston 4 in order to be able to move test material (not shown) with pressure towards the nozzle 54. In the shown movement 172, the test piston 4 is moved from a start position 151 end drive position 152 in an actuating manner by means of the drive unit 92 (see FIG. 1). During melting, the test material has settled from the experiment start position 158 to the starting position 151. On the first press-out path 166, test material is moved in the direction of the nozzle 54 and a part of the test material is pressed through the nozzle 54. At end drive position 152, which can also be called the second position of the test piston 4, a reduction of the actuating additional force 108 occurs. The movement 172 of the test piston 4 is caused when reaching a third position, the test start position 153, exclusively due to the test weight 72. Before reaching the test start position 153, the coupling unit 110 can be opened and the test weight 72 can be released by a lowering of the first arm end 81, so that the weight force 79 on the test piston 4 is present as the only driving force of the movement 172. The test stretch 168 in the test channel 38 is located between 153 the test start position 153 and a test end position 154, so a fourth position of the test piston 4. A pressing-out of the test mass, in particular by means of weight force 79, takes place on the test stretch 168. The passing of the test stretch 168 with the test piston 4 is accompanied by a time measurement by the time control unit 141 (see FIG. 1). Back to FIG. 4, at the test end position 154, the test end position 160 follows along the test channel 38 in which experiment end position 160 the heater 133 is switched off. Also, the test area end position 156 known from standards is located between the test end position 154 and the end position of the region for experiments 164. A second partial stretch as press-out path 167 in the test channel 38 is located between the test end position 154 and the test area end position of the region for experiments 164. On the press-out path 166, 167, test material that is not needed for a measurement of the flow time is pushed out quickly from the test channel 38 with the help of the actuating additional force 108.

FIG. 5 shows the flow test machine 202 with the test piston 204, whose pressing surface 212 is located in the test channel 238 on the test stretch 368 between the test start position 353 and the test end position 354. The movement of 372, shown as a movement direction arrow 372, through the test channel 238 only takes place under the effect of the weight force 279 of the test weight 272. The centering region 226" of the test piston 204 is connected to the centering section 278 of the test weight absorber. Therefore, a first centering area 226 and a second centering area 226" are provided on the test piston head 216. A focus of the test weight 272 is arranged on the test piston 204 in the central axis. The movement 372 between the starting position 351 and the end drive position 352 is reinforced on the press-out stretch by a drive unit 292, mediated by the arm 280 on the test piston head 216 so that the movement is 372 occurs with greater speed. The experiment start position 358 shows the originally present filling position of the test channel 238 with test material (not shown). A second partial stretch as a press-out path 367 follows the test end position 354 in the test channel 238. The second partial stretch extends from the starting position 351', which is allocated to an experiment end position 360, up to an end drive position 352', which is allocated to the end position of the region for experiments 364. The test area end position 356 marks a spacing of the test stretch 368 of the nozzle 254 which must be maintained according to applicable standards (in some countries). The nozzle 254 leads into an injection opening 267 of a press mold, which is an optional additional piece of equipment of the flow test machine 202. Investigations into the pressing of a test mass in a predetermined mold are thereby enabled. During the entire movement 372 of the test piston 204, a constant temperature is maintained in the test channel 238 by the heater 333. The coupling unit 310 held open by the second actuator 296 has the proximity sensor 328. The coupling unit 310 is positioned along the test stretch 368 by the drive unit 292 in front of the test piston head 216 in the movement direction 279 during the movement 372 of the test piston 204. The test piston 204 is monitored in the movement 372 by the path measurement device 330. The proximity sensor 328 allows the drive unit 292 to start the test piston head 216 after the test end position 354 and to couple it to the test piston head 216. The centering region 226 on the test piston head 216, which can be passed through the opening 284, facilitates the proximity. The test weight absorber 273 and the test weight bodies, such as the test weight body 274, have a larger diameter than the opening 284. The test weight absorber 273 is able to be listed by the test piston 204 on the arm 280.

In FIG. 6, the flow test machine 2 is in a second operating state 171. The test weight 72 is lifted by the drive unit 92 by means of the test cylinder 100 until the stop due to an actuating additional force 180' which is opposed in direction to the weight force 79 of the test weight 72. The test weight 72 lies on the arm 80 on the first arm end 81. In the end position 169 of the arm 80, the arm 80 on the second arm end 82 is rotatable with respect to the test cylinder 100. The pivot joint 90, due to which the arm 80 is rotatable, is fixed in the end position 169, in other words, locked. The coupling unit 110 is located in the release position 126.

As can be seen in FIG. 6—especially at the beginning of the process of cleaning—the head area 30 of the cleaning piston 28 is inserted in the bracket 112 at the centering region 26' of the cleaning piston head. Thus, the proximity sensor 128 signals that the holding elements, such as the holding element 122, can retract into the second coupling area 31. A cleaning cloth 32 is inserted between the cleaning piston 28 and the test channel 38. The cleaning cloth 32 can be pushed through the test channel 38 by the cleaning piston 28 by means of the drive unit 92. Test material 34 and impurities are thus absorbed by the inner wall of the test channel cylinder 40, and moved in the direction of the nozzle 54. The penetration depth of the cleaning piston 28 in the test channel 38 can be monitored with the path measurement device 130.

In FIG. 7, a pushed-through test channel 38 is shown, in which is found the cleaning piston 28. The nozzle insert 56, see, for example, FIG. 3, after loosening the nozzle holder 64 from the test channel 38 by means of the cleaning piston 28, is able to be extracted, similar to the course shown in FIG. 6. The cleaning piston 28 can penetrate the entire test channel 38, as FIG. 7 shows, and therein can carry a cleaning agent such as the cleaning cloth 32 (see FIG. 6). In FIG. 7, the nozzle holder 64 is pivoted away laterally with the nozzle slide 66 under the test channel 38, which is why the sectional drawing in FIG. 7 shows a protrusion of the nozzle holder 64 in front of the cleaning piston 28

In FIG. 7, the coupling unit 110 is located in a closed position 124, wherein the head region 30 of the cleaning piston 28 is fixed by the bracket 112 with the mold member 114 with respect to the centering region 26'. The arm 80 (illustrated in sections) is in this case located near an end position 169', while the piston 28 carries out a movement 172 which leads the cleaning piston 28 into and, in stretches, through the test channel 38. The movement 172 is driven by the weight force 79 and the actuating additional force 108 in the same direction, wherein a first operating state is present 170. Upon reaching the end position 169', a second operating state 171' is occupied in that the actuating additional force 108" is reversed in direction and the weight force 79 is applied increasingly in amount so that a movement 172' is performed. The force vectors 79, 108, 108" are only next to one another and at a distance from the central axis 46, the position of which is drawn in in FIG. 1, for simplicity of the depiction. There is no torque that could tip the cleaning piston 28 from the central axis 46. The movement 172' guides the arm 80 back from the end position 169'. Subsequently, the cleaning piston 28 can be replaced again by a test piston (such as test piston 4 in FIG. 1).

In a further embodiment of a flow test machine similar to the flow test machines 2 and 202, the arm 80 or the coupling unit 110, preferably have a rotary element which is able to be driven by a motor or actuator, in particular in connection with a pivot joint. With a rotary element, for example by means of the drive unit 92, the cleaning piston 28 can be rotatable, like a drill.

Figure 8:
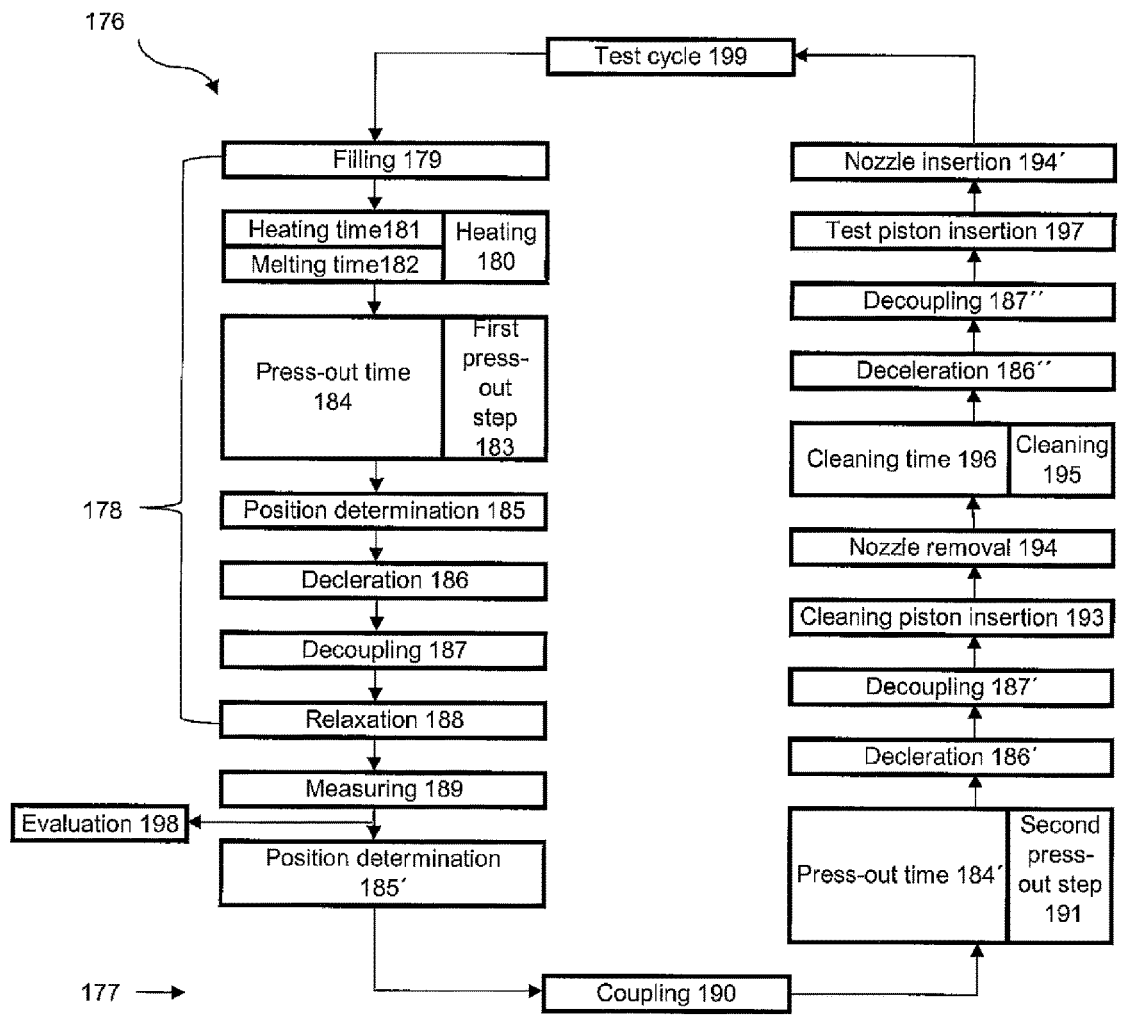
FIG. 8 shows a schematic course of a flow test method having a cleaning method.

Steps of a flow test method 176 in schematic enumeration, which are, for example, carried out in a melt viscosity testing, are shown in FIG. 8. The flow test method 176 is able to be carried out in combination with a cleaning process 177 as a test cycle 199 several times in succession. The flow test method 176 begins with a measurement preparation step 178, to which several partial steps can be allocated. In a filling step 179, the test mass is portioned for a flow test and placed in a flow test machine 2 (e.g. according to FIG. 1). A heating step 180 follows to a target temperature with a heating time 181 and a melting time 182. In the melting time 182, the test mass achieves a stated which is able to be tested for ability to flow. The heating step 180 is continued until the point in time at which at least one measuring step 189 is rendered so that during the flow test method 176 temperature conditions are predominant which are as constant as possible. The melting time 182 is followed by a first press-out step 183, wherein the press-out time 184 is shortened by application of an actuating additional force from a drive unit, such as the drive unit 92 (see FIG. 1), with regard to a press-out by a weight force. After the first press-out step 183 preferably a position determination 185 of the test piston is carried out, such as the test piston 4 (see FIG. 1), and a deceleration step 186, in which at least the actuating additional force is withdrawn. It can also be said that in the deceleration step 186, an actuator of a drive unit is switched to a passive operation, which in particular is free of pressure difference. The decoupling step 187 follows the deceleration step 186, in which a, in particular frictional or firm, connection between a drive unit, such as the drive unit 92 shown in FIG. 1, and the test piston, such as the test piston 4 shown in FIG. 1, is separated. The decoupling step 187 preferably comprises that the drive unit 92, which has unloaded the test weight on the test piston 4, is positioned without the test weight in a second end position or is driven at least at a predetermined distance to the test piston head. The distance can, for example, be checked using a proximity sensor on an arm. A relaxation step 188 follows, in which flow conditions in the test mass still located in the flow test method, so in particular the test mass volume, are equalized under the effect of a test weight on the test mass, such as, for example, the temperature and density of the test mass. After the relaxation step 188, the measurement step 189 is performed, which includes a test stretch. A path-time measurement takes place on the test stretch. After completion of the measuring step 189, the recorded data can be analyzed directly in an evaluation step 198. Further measurements can, however, also take place in the evaluation step 198, such as a thread length measurement, a weighing, spectrometric investigations or chemical analysis of the test mass pressed out in the measurement step 189. Such data collection and measurement steps, which are connected to the measuring step 189, can be summarized in an evaluation step 198. The end of the measurement step 189 is associated with a position determination 185', which can also occur as part of a path stretch measurement.

Further steps which follow the position determination 185' can be attributed to a cleaning method 177. With the help of the position determining 185', a proximity and coupling step 190 is executed. The drive unit, such as the drive unit 92 shown in FIG. 1, is brought into a frictional and firm connection with the test piston, in particular with the test piston head. A second press-out step 191 follows, wherein the drive unit applies an actuating additional force to the test piston. The test piston is hereby moved with a speed which is increased as compared to the effect of the weight force. The press-out time 184' is thus shortened. The second press-out step 191 comes to an end with a deceleration step 186', in which the actuating additional force is withdrawn. It is also possible to switch the actuating additional force after a quantitative withdrawal in the direction, to compensate for the weight force of the test weight. Therefore a loading in the area of the nozzle, such as the nozzle 54 (as shown in FIG. 3), can be reduced. In the flow testing method 176, a decoupling step 187' now takes place, in which the frictional and firm connection between drive unit and test piston is opened and the drive unit together with the test weight is positioned in a first end position. It is also possible, in an alternative method, to remove the test piston with the drive unit from the test channel. To continue the cleaning method 177, the test piston is now removed or deposited in a test piston holder and a cleaning piston is used according to a step marked by 193. In other words, the cleaning piston, in particular the cleaning piston head, is connected to the single drive unit, which as works in the flow testing method 176. Thus, the cleaning piston sits in front of the filling opening of the test channel. The nozzle removal 194 follows, wherein a path is released through the test channel. In the cleaning step 195, which can also be described as a second cleaning step, the cleaning piston is pushed with the help of the actuating additional force through the test channel in a cleaning time 196 shortened compared to the effect of the weight force. It is possible, as shown in FIG. 6, to carry a cloth 32 laid on the filling opening in front of the cleaning piston 28 through the test channel 38. Therefore even caked dirt particles or traces of dirt can be eliminated from the test channel 38. After the cleaning piston 28 has be driven through the test channel 38, a deceleration step 186" takes place, wherein the cleaning piston 28 is brought to a stand-still by switching the actuating additional force and the quantitative alignment to the weight force of the test weight of the cleaning piston 28 thereof. Then it is possible to undertake a decoupling step 187", and to separate the firm and frictional connection between cleaning piston and drive unit. In an alternative to the cleaning step 177 it is also possible to carry out the decoupling of the cleaning piston 28 only after the withdrawal of the drive unit into the first end position. The withdrawal of the drive unit and the removal of the cleaning piston 28, in particular from the test channel 38, and an insertion of a test piston (see step 197) follows the decoupling step 187" in the cleaning method 177. The method is ready for continuation in a test cycle 199 with the insertion of the nozzle according to step 194'.

Using the method described above and with the aid of the flow test machine 2 described above, in particular melt viscosity tests can be executed with great time saving and high precision. It is possible to form alternatives of method courses, in which individual or multiple method steps or partial steps are left out, added to or exchanged.

The embodiment possibilities shown in the individual figures can also connect with each other in any form. For example it is adduced, that a flow test machine can have several test pistons 4, the heating device 133, 333 may be shorter or longer in relation to the test channel 38, 238 and that the nozzle 54, 254 can also have more than only two diameters along its opening.

LIST OF REFERENCE NUMERALS 2, 202 Flow test machine
3 Base
4, 204 Test Piston
6 Piston diameter
8 Piston length, in particular test piston length
9 Length mark
10 Test piston axis
12, 212 Pressing surface
14 Sealing area
16, 216 Test piston head
20 First coupling area
24 Support region
26, 26', 226, 226" Centering area, especially of a piston head
28 Service piston, in particular cleaning piston
30 Head region, in particular cleaning piston head
31 Second coupling region
32 Cleaning agent, especially cloth
34 Test material, in particular remains
36 Test space
38, 238 Test channel
40 Test channel cylinder
42 Channel diameter
44 Channel length
46 Central axis
48 Outflow side
50 Filling side, in particular filling opening, such as a filling cone
52 Outlet opening, in particular end area of the test channel
54, 254 Nozzle, in particular press-out nozzle
56 Nozzle insert
58 Nozzle input diameter
60 Nozzle output diameter
62 Nozzle channel length
64 Nozzle holder
66 Nozzle slide
267 Injection opening, especially mold
70 Press-out material chamber, in particular separating door
72, 272 Test weight
73, 273 Test weight receiver, in particular first test weight body
74, 274 Test weight body, in particular second
75 Test weight body, in particular third
77, 77' Support region
78, 78', 78", 278 Centering area, in particular of the test weight
79, 279 Weight force of the test weight, in particular weight force direction
80, 280 Arm, in particular movable arm
81 First arm end
82 Second Arm end
84, 284 Opening
85 Test channel side of the arm, particularly of the arm end
86 Test weight side of the arm, particularly of the arm end
88 Stop, in particular anti-rotation stop
89, 89' Stop, in particular end position stop
90 Pivot joint, in particular rotary joint
92, 292 Drive unit
94 First actuator
96, 296 Second actuator
98 Speed control
100 Test cylinder
102 First control side
104 Second control side
106 Travel path
108, 108', 108" Actuating additional force
110, 310 Coupling unit
112 Bracket
114, 114' Mold element
115, 115' Support surface
116 Clamping unit
120 Lock, especially electromagnetic or pneumatic lock, preferably a hydraulic lock
122 Holding element
124, 124' Closed position
126 Released position
128, 328 Proximity sensor or approximation sensor
130, 330 Path measurement device, in particular piston position measurement device
131 Measurement lever
132 Stretch sensor
133, 333 Heating device
134 Thermal insulating body
136 Temperature measuring devices, particularly sensors
138 Pressure control unit, in particular pressure regulation unit
139 Adjustable foot
140 Control unit, in particular control electronics
141 Time control unit
142 Deflection device, in particular switch of a movement element
144 Switching valve, in particular switching valve of change-over type
146 Switching valve case
148 First switching position, in particular of a coupling unit
150 Second switching position, in particular of a coupling unit
151, 351, 351' First position of the test piston, in particular starting position
152, 352, 352' Second position of the test piston, in particular end drive position
153, 353 Third position of the test piston, in particular test start position
154, 354 Fourth position of the test piston, in particular test end position
156, 356 Test area end position
158, 358 Experiment start position
160, 360 Experiment end position
164, 364 End position of a region of experiments
166, 366 Stretch, in particular first partial stretch, preferably press-out path
167, 367 Stretch, in particular second partial stretch, preferably press-out path
168, 368 Test stretch
169, 169' End position, in particular stop position
170 First operating state
171, 171' Second operating state
172, 172', 372 Movement, in particular direction of motion of a piston
174 First direction, especially of a force
175 Second direction, especially of a force
176 Flow test method, in particular melting viscosity test,
177 Cleaning method, preferably for a flow test machine 178 Measurement preparation step
179 Filling step
180 Heating step
181 Heating time
182 Melting time
183 First press-out step
184, 184' Press-out time
185, 185' Position determination, in particular determining a retracted path
186, 186', 186" Deceleration step, in particular actuator switch
187 Decoupling step, in particular positioning of the drive unit, in particular without test weight, in a second end position
187', 187" Decoupling step, in particular positioning of the drive unit, in particular with test weight, in a first end position
188 Relaxation step
189 Measuring step, in particular path-time measurement
190 Proximity and coupling step
191 Second press-out step, in particular first cleaning step
193 Removal of the test piston and insertion of a cleaning piston
194 Nozzle removal
194' Insert nozzle
195 Cleaning step, in particular second cleaning step
196 Cleaning time
197 Removal of the cleaning piston and insertion of a test piston
198 Evaluation step, in particular calculation step
199 Test cycle
A Cut-out, comprising first arm end and test weight
B Cut-out, comprising nozzle on the downstream side of the test channel

The invention claimed is:
1. A flow test machine comprising:
a test piston,
a test channel,
a test weight, and
a drive unit,
wherein the drive unit is connected to a bracket that is configured for being switched into a closed position and a release position; and
wherein a weight force of the test weight is applied to the test piston and the test piston is moved through the test channel with the aid of the weight force,
wherein in a drive state, the drive unit is configured for raising or lowering the test weight, and
wherein, on at least one stretch along the test channel between a first, starting position of the test piston and a second, end position of the test piston the weight force is applied to the test piston in combination with an additional actuating force by the drive unit during a movement of the test piston in a first direction of the weight force, said movement being accelerated in comparison to movement of the test piston under an effect of the weight force alone.
2. The flow test machine as claimed in claim 1, wherein the drive unit has a coupling unit which is configured to apply the additional actuating force to the test piston, wherein the coupling unit has a first switching position wherein the additional actuating force is separated from the test piston, and wherein the coupling unit has a second switching position wherein the additional actuating force is applied to the test piston via the coupling unit.

3. The flow test machine as claimed in claim 1 wherein the test piston has a test piston head having a first coupling area for the drive unit, said first coupling area being connected to a carrier region for the test weight on one end of the test piston.
4. The flow test machine as claimed in claim 1, wherein a piston position measurement device is provided, and wherein the piston position measurement device is configured to provide a positioning signal indicating a position of the test piston for controlling a holding element, and wherein the holding element is located on at least one of the group consisting of: the test piston, the test weight, and a test weight absorber.
5. The flow test machine as claimed in claim 1, wherein the flow test machine comprises a heating device and a time control unit, and wherein the time control unit is configured to determine switching times of the heating device in the course of a single process step.
6. The flow test machine as claimed in claim 1, wherein the drive state of the flow test machine is a first operating state and wherein, in a second operating state of the flow test machine, the drive unit is configured to generate a force in a second direction that is opposed to the weight force by means of a deflection device.
7. The flow test machine as claimed in claim 1, wherein the drive unit is configured such that one of the first position and second position is a test region end position adjacent a downstream side of the test channel.
8. The flow test machine as claimed in claim 1, wherein the flow test machine further comprises a control unit configured to control an actuator of the bracket such that the test piston has, between the first, starting position and the second, end position, a third position and a fourth position, wherein the third position is a test starting position and is separated from the fourth position by a test stretch, and wherein the fourth position is a test end position.
9. The flow test machine as claimed in claim 1, further comprising an arm which is configured to be moved by the drive unit in a test direction, wherein the arm receives the test weight, and wherein a first arm end has an opening which is configured to be disposed about the test piston.
10. The flow test machine as claimed in claim 9, wherein the test piston includes a test piston head and wherein a holding area for the test piston head is present on an underside of the first arm end,
and wherein the arm is pivotable in a plane in the first, starting position or the second, end position, and wherein the arm is movable to replace a first test weight with a second test weight.
11. The flow test machine as claimed in claim 1, wherein the drive unit is configured to apply the weight force and the additional actuating force to the test piston on at least two partial stretches of the test channel which are spaced apart from each other.
12. The flow test machine as claimed in claim 1, wherein the drive unit has an inductive proximity sensor for the detection of a test piston position.
13. The flow test machine as claimed in claim 1, wherein the bracket is an electromagnetic or pneumatic lock which is configured to fix the test piston.
14. The flow test machine as claimed in claim 1, wherein the second position is adjacent a nozzle bordering the test channel and one stretch is within two centimeters from the second position.
15. The flow test machine as claimed in claim 1, wherein the bracket comprises an approximation sensor configured to detect a test piston position.

16. The flow test machine as claimed in claim 1, wherein the bracket comprises a clamping unit which is configured to provide a reproducible orientation of the test piston.

17. A flow test machine comprising:
a test piston,
a test channel,
a test weight,
a drive unit, and
a pressure control unit;
wherein a weight force of the test weight is applied to the test piston and the test piston is moved through the test channel with the aid of the weight force,
wherein in a drive state, the drive unit is configured for raising or lowering the test weight, and
wherein, on at least one stretch along the test channel between a first, starting position of the test piston and a second, end position of the test piston the weight force is applied to the test piston in combination with an additional actuating force by the drive unit during a movement of the test piston in a first direction of the weight force, said movement being accelerated in comparison to movement of the test piston under an effect of the weight force alone; and
wherein the pressure control unit is configured to regulate the additional actuating force by a pressure and wherein the pressure control unit is configured to adjust the pressure.

18. The flow test machine as claimed in claim 17, wherein the pressure control unit is configured to predetermine a maximum pressure to be applied to the test piston by the drive unit, and wherein the pressure is a pneumatic pressure, a hydraulic pressure, an electrically generated pressure, or a mechanically generated pressure.

19. A flow test machine comprising:
a test piston,
a test channel,
a test weight, and
a drive unit,
wherein a weight force of the test weight is applied to the test piston and the test piston is moved through the test channel with the aid of the weight force,
wherein in a drive state, the drive unit is configured for raising or lowering the test weight,
wherein, on at least one stretch along the test channel between a first, starting position of the test piston and a second, end position of the test piston the weight force is applied to the test piston in combination with an additional actuating force by the drive unit during a movement of the test piston in a first direction of the weight force, said movement being accelerated in comparison to movement of the test piston under an effect of the weight force alone;
wherein the test piston has, between the first, starting position and the second, end position, a third position and a fourth position, wherein the third position is a test starting position and is separated from the fourth position by a test stretch, and wherein the fourth position is a test end position; and
wherein the flow test machine is configured to reverse the direction of the additional actuating force before arriving at the second position to brake the test piston before reaching one end of a press-out path.

20. A flow test machine comprising:
a test piston,
a test channel,
a test weight, and
a drive unit,
wherein a weight force of the test weight is applied to the test piston and the test piston is moved through the test channel with the aid of the weight force,
wherein in a drive state, the drive unit is configured for raising or lowering the test weight, and
wherein, on at least one stretch along the test channel between a first, starting position of the test piston and a second, end position of the test piston the weight force is applied to the test piston in combination with an additional actuating force by the drive unit during a movement of the test piston in a first direction of the weight force, said movement being accelerated in comparison to movement of the test piston under an effect of the weight force alone; and
wherein at least one stop is provided on the drive unit and wherein the test piston is configured to be decoupled from the drive unit when the drive unit is in a stop position.

* * * * *